(12) United States Patent
Broughton et al.

(10) Patent No.: US 6,479,506 B1
(45) Date of Patent: Nov. 12, 2002

(54) TRIAZOLO-PYRIDINE DERIVATIVES AS LIGANDS FOR GABA RECEPTORS

(75) Inventors: Howard Barff Broughton, Bishops Stortford (GB); Jose Luis Castro Pineiro, Bishops Stortford (GB); Ian James Collins, Ware (GB); Leslie Joseph Street, Little Hallingbury (GB)

(73) Assignee: Merck Sharp & Dohme Ltd., Hoddesdon (GB)

( * ) Notice: Subject to any disclaimer, the term of this patent is extended or adjusted under 35 U.S.C. 154(b) by 0 days.

(21) Appl. No.: 09/674,894

(22) PCT Filed: Jun. 9, 1999

(86) PCT No.: PCT/GB99/01838

§ 371 (c)(1),
(2), (4) Date: Nov. 7, 2000

(87) PCT Pub. No.: WO99/65904

PCT Pub. Date: Dec. 23, 1999

(30) Foreign Application Priority Data

Jun. 16, 1998 (GB) .............................................. 9813005
Sep. 10, 1998 (GB) .............................................. 9819756

(51) Int. Cl.[7] .................. A61K 31/4353; C07D 471/04
(52) U.S. Cl. ........................................ 514/300; 546/117
(58) Field of Search ............................ 546/117; 514/300

(56) References Cited

U.S. PATENT DOCUMENTS 5,166,209 A    11/1992    Kelley

FOREIGN PATENT DOCUMENTS

| EP | 399 653 | 11/1990 |
| WO | WO 98/04559 | 2/1998 |
| WO | WO 98/04560 | 2/1998 |

OTHER PUBLICATIONS

Wafford et al., Mol. Pharmacol., 50: 670–678 (1996).
Dawson et al., Psychopharmacology, 121: 109–117 (1995).
Bayley et al., J. Psychopharmacol., 10: 206–213 (1996).
Bristow et al., J.Pharmacol. Exp. Ther., 279: 492–501 (1996).

*Primary Examiner*—Patricia L. Morris
(74) *Attorney, Agent, or Firm*—J. Eric Thies; Melvin Winokur

(57) ABSTRACT

Substituted or 6,7-ring fused 1,2,3-triazolo[4,5-b]pyridine derivatives are selective ligands for $GABA_A$ receptors useful in the treatment of disorders of the central nervous system.

7 Claims, No Drawings

TRIAZOLO-PYRIDINE DERIVATIVES AS LIGANDS FOR GABA RECEPTORS

This is an application under 35 U.S.C. 371 of PCT/GB99/01838 and claims priority from Great Britain Application No. 9813005.7, filed Jun. 16, 1998 and Great Britain Application No. 9819756.9, filed Sep. 10, 1998.

The present invention relates to a class of substituted triazolo-pyridine derivatives and to their use in therapy. More particularly, this invention is concerned with substituted 1,2,3-triazolo[4,5-b]pyridine derivatives which are ligands for $GABA_A$ receptors and are therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six α subunits, four β subunits, three γ subunits, one δ subunit, one ε subunit and two ρ subunits.

Although knowledge of the diversity of the $GABA_A$ receptor gene family represents a huge step forward in our understanding of this ligand-gated ion channel, insight into the extent of subtype diversity is still at an early stage. It has been indicated that an α subunit, a β subunit and a γ subunit constitute the minimum requirement for forming a fully functional $GABA_A$ receptor expressed by transiently transfecting cDNAs into cells. As indicated above, δ, ε and ρ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one α, one β and one γ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $α1β2γ2$, $α2β2/3γ2$, $α3βγ2/3$, $α2βγ1$, $α5β3γ2/3$, $α6βγ2$, $α6βδ$ and $α4βδ$. Subtype assemblies containing an α1 submit are present in most areas of the brain and are thought to account for over 40% of $GABA_A$ receptors in the rat. Subtype assemblies containing α2 and α3 subunits respectively are thought to account for about 25% and 17% of $GABA_A$ receptors in the rat. Subtype assemblies containing an α5 subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the α1 subunit in combination with a β subunit and γ2. This is the most abundant $GABA_A$ receptor subtype, and is believed to represent almost half of all $GABA_A$ receptors in the brain.

Two other major populations are the $α2βγ2$ and $α3βγ2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at $α1βγ2$, $α2βγ2$ or $αa3βγ2$ subunits will possess desirable anxiolytic properties. Compounds which are modulators of the benzodiazepine binding site of the $GABA_A$ receptor by acting as BZ agonists are referred to hereinafter as "$GABA_A$ receptor agonists". The α1-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the α1 subunit. Accordingly, it is considered that $GABA_A$ receptor agonists which interact more favourably with the α2 and/or α3 subunit than with α1 will be effective in the treatment of anxiety with a reduced propensity to cause sedation. Also, agents which are antagonists or inverse agonists at al might be employed to reverse sedation or hypnosis caused by α1 agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; and disorders of circadian rhythm, e.g. in subjects suffering from the effects of jet lag or shift work.

Further disorders for which selective ligands for $GABA_A$ receptors may be of benefit include pain and nociception; emesis, including acute, delayed and anticipatory emesis, in particular emesis induced by chemotherapy or radiation, as well as post-operative nausea and vomiting; eating disorders including anorexia nervosa and bulimia nervosa; premenstrual syndrome; muscle spasm or spasticity, e.g. in paraplegic patients; and hearing loss. Selective ligands for $GABA_A$ receptors may also be effective as pre-medication prior to anaesthesia or minor procedures such as endoscopy, including gastric endoscopy.

WO 98/04559 describes a class of substituted and 7,8-ring fused 1,2,4-triazolo[4,3-b]pyridazine derivatives which are stated to be selective ligands for $GABA_A$ receptors beneficial in the treatment and/or prevention of neurological disorders including anxiety and convulsions. There is in that publication, however, no disclosure nor any suggestion that the central triazolo-pyridazine ring system can be replaced by any other ring system. In particular, there is no disclosure nor any suggestion therein that the specified triazolo-pyridazine ring system can be replaced by a 1,2,3-triazolo[4,5-b]pyridine ring system.

SUMMARY OF THE INVENTION

The present invention is directed to compounds according to Formula (I) or a pharmaceutically acceptable salt thereof that are GABA$_A$ ligands useful in the treatment of disorders of the central nervous system:

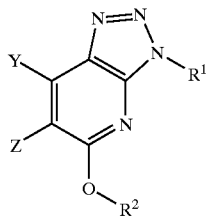

DETAILED DESCRIPTION OF THE INVENTION

The present invention provides a class of triazolo-pyridine derivatives which possess desirable binding properties at various GABA$_A$ receptor subtypes. The compounds in accordance with the present invention have good affinity as ligands for the α2 and/or α3 subunit of the human GABA$_A$ receptor. The compounds of this invention may interact more favourably with the α2 and/or α3 subunit than with the α1 subunit. Desirably, the compounds of the invention will exhibit functional selectivity in terms of a selective efficacy for the α2 and/or α3 subunit relative to the α1 subunit.

The compounds of the present invention are GABA$_A$ receptor subtype ligands having a binding affinity (K$_i$) for the α2 and/or α3 subunit, as measured in the assay described hereinbelow, of 100 nM or less, typically of 50 nM or less, and ideally of 10 nM or less. The compounds in accordance with this invention may possess at least a 2-fold, suitably at least a 5-fold, and advantageously at least a 10-fold, selective affinity for the α2 and/or α3 subunit relative to the α1 subunit. However, compounds which are not selective in terms of their binding affinity for the α2 and/or α3 subunit relative to the al subunit are also encompassed within the scope of the present invention; such compounds will desirably exhibit functional selectivity in terms of a selective efficacy for the α2 and/or α3 subunit relative to the α1 subunit.

The present invention provides a compound of formula I, or a salt or prodrug thereof:

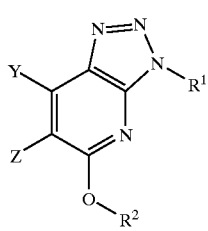

wherein
Y represents hydrogen or C$_{1-6}$ alkyl; and
Z represents C$_{1-6}$ alkyl, C$_{3-7}$ cycloalkyl, C$_{4-7}$ cycloalkenyl, C$_{6-8}$ bicycloalkyl, aryl, C$_{3-7}$ heterocycloalkyl, heteroaryl, C$_{2-7}$ alkoxycarbonyl or di(C$_{1-6}$)alkylamino, any of which groups may be optionally substituted; or Y and Z are taken together with the two intervening carbon atoms to form a ring selected from C$_{5-9}$ cycloalkenyl, C$_{6-10}$ bicycloalkenyl, tetrahydropyridinyl, pyridinyl and phenyl, any of which rings may be optionally benzo-fused and/or substituted;

R$^1$ represents C$_{3-7}$ cycloalkyl, phenyl, furyl, thienyl or pyridinyl, any of which groups may be optionally substituted; and R$^2$ represents C$_{3-7}$ cycloalkyl(C$_{1-6}$)alkyl, aryl(C$_{1-6}$)alkyl or heteroaryl(C$_{1-6}$)alkyl, any of which groups may be optionally substituted.

Where Y and Z are taken together with the two intervening carbon atoms to form a ring, the resulting compounds of formula I above incorporate the relevant cycloalkenyl, bicycloalkenyl, tetrahydropyridinyl, pyridinyl or phenyl ring fused to the central triazolo-pyridazine ring system as depicted in formula I.

Where Y and Z are taken together with the two intervening carbon atoms to form a C$_{5-9}$ cycloalkenyl ring, this ring may be a cyclopentenyl, cyclohexenyl, cycloheptenyl, cyclooctenyl or cyclononenyl ring, suitably cyclohexenyl or cycloheptenyl.

Where Y and Z are taken together with the two intervening carbon atoms to form a C$_{6-10}$ bicycloalkenyl ring, this ring may be a bicyclo[2.1.1]hex-2-enyl, bicyclo[2.2.1]hept-2-enyl, bicyclo[2.2.2]oct-2-enyl, bicyclo[3.2.2]non-6-enyl or bicyclo[3.3.2]dec-9-enyl ring, suitably bicyclo[2.2.1]hept-2-enyl, bicyclo[2.2.2]oct-2-enyl or bicyclo[3.2.2]non-6-enyl, and especially bicyclo[2.2.2]oct-2-enyl.

Where Y and Z are taken together with the two intervening carbon atoms to form a ring, this ring may be optionally benzo-fused. By way of illustration, Y and Z taken together with the two intervening carbon atoms may represent a benzo-fused cyclohexenyl ring, whereby the resulting ring is dihydronaphthyl.

The groups Y, Z, R$^1$ and R$^2$ may be unsubstituted, or substituted by one or more, suitably by one or two, substituents. In general, the groups Y, Z, R$^1$ and R$^2$ will be unsubstituted or monosubstituted. Examples of optional substituents on the groups Y, Z, R$^1$ and R$^2$ include C$_{1-6}$ alkyl, aryl(C$_{1-6}$)alkyl, pyridyl(C$_{1-6}$)alkyl, halogen, halo(C$_{1-6}$) alkyl, cyano, cyano(C$_{1-6}$)alkyl, hydroxy, hydroxymethyl, C$_{1-6}$ alkoxy, C$_{3-7}$ cycloalkyl(C$_{1-6}$)alkoxy, C$_{3-7}$ cycloalkoxy, amino(C$_{1-6}$)alkyl, di(C$_{1-6}$)alkylamino(C$_{1-6}$)alkyl, di(C$_{1-6}$)alkylaminocarbonyl(C$_{1-6}$)alkyl, N-(C$_{1-6}$)alkylpiperidinyl, pyrrolidinyl(C$_{1-6}$)alkyl, piperazinyl(C$_{1-6}$)alkyl, morpholinyl(C$_{1-6}$)alkyl, di(C$_{1-6}$)alkylmorpholinyl(C$_{1-6}$)alkyl and imidazolyl(C$_{1-6}$)alkyl. Representative substituents include C$_{1-6}$ alkyl, aryl(C$_{1-6}$)alkyl, halogen, cyano, hydroxy, hydroxymethyl, C$_{1-6}$ alkoxy and C$_{3-7}$ cycloalkyl(C$_{1-6}$) alkoxy. Specific substituents include C$_{1-6}$ alkyl, halogen and C$_{1-6}$ alkoxy, particularly methyl, ethyl, n-propyl, fluoro or ethoxy, and especially methyl or fluoro.

As used herein, the expression "C$_{1-6}$ alkyl" includes methyl and ethyl groups, and straight-chained or branched propyl, butyl, pentyl and hexyl groups. Particular alkyl groups are methyl, ethyl, n-propyl, isopropyl, tert-butyl, 1,1-dimethylpropyl and 2,2-dimethylpropyl. Derived expressions such as "C$_{1-6}$ alkoxy" are to be construed accordingly.

Typical C$_{3-7}$ cycloalkyl groups include cyclopropyl, cyclobutyl, cyclopentyl and cyclohexyl.

The expression "C$_{3-7}$ cycloalkyl(C$_{1-6}$)alkyl" as used herein includes cyclopropylmethyl, cyclobutylmethyl, cyclopentylmethyl and cyclohexylmethyl.

Typical $C_{4-7}$ cycloalkenyl groups include cyclobutenyl, cyclopentenyl and cyclohexenyl.

Typical aryl groups include phenyl and naphthyl, preferably phenyl.

The expression "aryl($C_{1-6}$)alkyl" as used herein includes benzyl, phenylethyl, phenylpropyl and naphthylmethyl.

Suitable heterocycloalkyl groups include azetidinyl, pyrrolidinyl, piperidinyl, piperazinyl, morpholinyl and thiomorpholinyl groups.

Suitable heteroaryl groups include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl($C_{1-6}$)alkyl" as used herein includes furylmethyl, furylethyl, thienylmethyl, thienylethyl, pyrazolylmethyl, oxazolylmethyl, oxazolylethyl, isoxazolylmethyl, thiazolylmethyl, thiazolylethyl, imidazolylmethyl, imidazolylethyl, benzimidazolylmethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridinylmethyl, pyridinylethyl, pyridazinylmethyl, pyrimidinylmethyl, pyrazinylmethyl, quinolinylmethyl, isoquinolinylmethyl and quinoxalinylmethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, Y represents hydrogen or methyl, especially hydrogen.

Representative values for the substituent Z include methyl, ethyl, isopropyl, tert-butyl, 1,1-dimethylpropyl, 2,2-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, fluorophenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino. Specific values of Z include tert-butyl, 2,2-dimethylpropyl, cyclobutyl, phenyl, 2-fluorophenyl, 3-fluorophenyl, 4-fluorophenyl, 2-furyl, 3-furyl, 2-thienyl, 3-thienyl and methoxyearbonyl.

Illustrative values for the substituent Z include methyl, ethyl, isopropyl, tert-butyl, 1,1-dimethylpropyl, 2,2-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino. Particular values of Z include 2,2-dimethylpropyl, cyclobutyl, phenyl, 2-thienyl, 3-thienyl and methoxycarbonyl.

Examples of suitable values for the substituent Z include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino. Typical values include methyl, ethyl, phenyl, piperidinyl, pyridinyl, thienyl and methoxycarbonyl, especially phenyl or methoxycarbonyl.

In a particular embodiment, the substituent Z represents $C_{3-7}$ cycloalkyl, either unsubstituted or substituted by $C_{1-6}$ alkyl, especially methyl. Favourably, Z represents cyclobutyl.

When Y and Z are taken together with the two intervening carbon atoms to form a ring, representative compounds according to the invention include those of structure IA to IL:

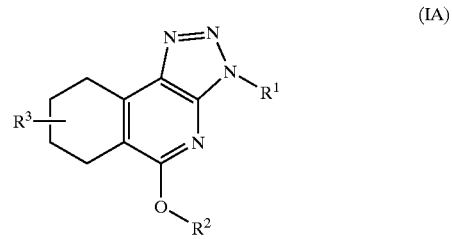

(IA)

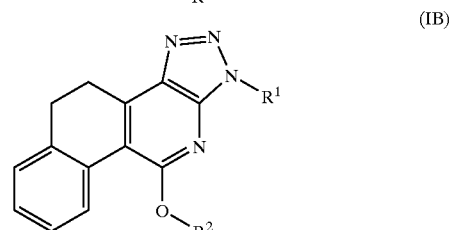

(IB)

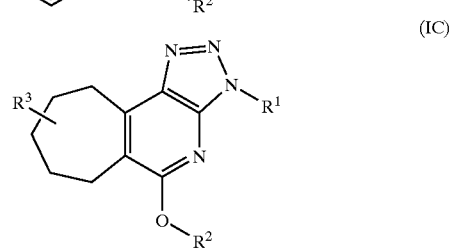

(IC)

-continued

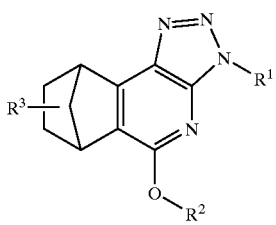
(ID)

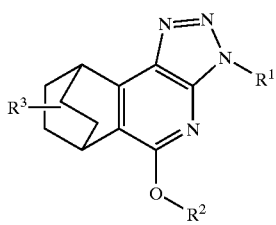
(IE)

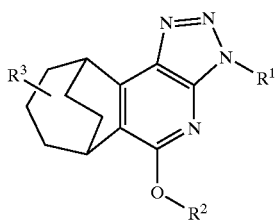
(IF)

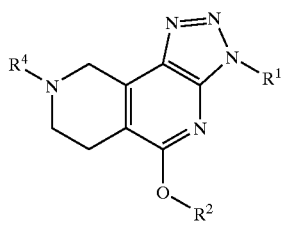
(IG)

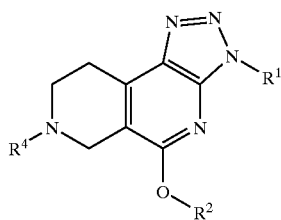
(IH)

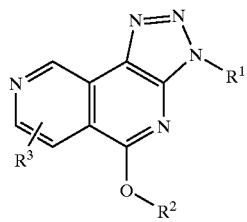
(IJ)

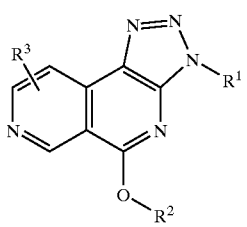
(IK)

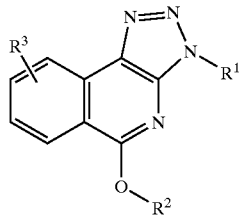
(IL)

wherein $R^1$ and $R^2$ are as defined above;

$R^3$ represents hydrogen, $C_{1-6}$ alkyl, aryl($C_{1-6}$)alkyl, halogen, cyano, hydroxy, hydroxymethyl or $C_{1-6}$ alkoxy; and $R^4$ represents hydrogen or $C_{1-6}$ alkyl.

Suitably, $R^3$ represents hydrogen or $C_{1-6}$ alkyl, especially hydrogen or methyl.

Suitably, $R^4$ represents hydrogen or methyl.

Favoured triazolo-pyridine derivatives according to the present invention include the compounds represented by formula IL as depicted above.

Examples of typical optional substituents on the group $R^1$ include methyl, fluoro and methoxy.

Illustrative values of $R^1$ include cyclopropyl, phenyl, methylphenyl, fluorophenyl, difluorophenyl, methoxyphenyl, (fluoro)(methoxy)phenyl, furyl, thienyl, methyl-thienyl and pyridinyl. Specific values of $R^1$ include phenyl, fluorophenyl, difluorophenyl and (fluoro)(methoxy) phenyl.

Representative values of $R^1$ include cyclopropyl, phenyl, methylphenyl, fluorophenyl, difluorophenyl, methoxyphenyl, furyl, thienyl, methyl-thienyl and pyridinyl. Suitably, $R^1$ represents phenyl, fluorophenyl, difluorophenyl or trifluorophenyl. In particular, $R^1$ may represent phenyl, fluorophenyl or difluorophenyl. More particularly, $R^1$ may represent unsubstituted or monosubstituted phenyl. Most particularly, $R^1$ represents phenyl or fluorophenyl.

Suitably, $R^2$ represents aryl($C_{1-6}$)alkyl or heteroaryl($C_{1-6}$) alkyl, either of which groups may be optionally substituted.

Suitable values for the substituent $R_2$ in the compounds according to the invention include cyclohexylmethyl, benzyl, pyrazolylmethyl, isoxazolylmethyl, thiazolylmethyl, thiazolylethyl, imidazolylmethyl, benzimidazolylmethyl, oxadiazolylmethyl, triazolylmethyl, tetrazolylmethyl, pyridinylmethyl, pyridazinylmethyl, pyrimidinylmethyl, pyrazinylmethyl, quinolinylmethyl, isoquinolinylmethyl and quinoxalinylmethyl, any of which groups may be optionally substituted by one or more substituents.

Suitably, $R_2$ represents an optionally substituted triazolyl-methyl or pyridinylmethyl group. More particularly, $R_2$ represents an optionally substituted triazolylmethyl group.

Examples of suitable optional substituents on the group $R_2$ include $C_{1-6}$ alkyl, aryl($C_{1-6}$)alkyl, pyridyl($C_{1-6}$)alkyl, halogen, halo($C_{1-6}$)alkyl, cyano, cyano($C_{1-6}$)alkyl, hydroxymethyl, $C_{1-6}$ alkoxy, $C_{3-7}$ cycloalkyl($C_{1-6}$)alkoxy, amino($C_{1-6}$)alkyl, di($C_{1-6}$)alkylamino($C_{1-6}$)alkyl, di($C_{1-6}$) alkylaminocarbonyl($C_{1-6}$)alkyl, N-($C_{1-6}$)alkylpiperidinyl, pyrrolidinyl($C_{1-6}$)alkyl, piperazinyl($C_{1-6}$)alkyl, morpholinyl ($C_{1-6}$)alkyl and di($C_{1-6}$)alkylmorpholinyl($C_{1-6}$)alkyl.

Specific illustrations of particular substituents on the group $R^2$ include methyl, ethyl, n-propyl, benzyl, pyridinylmethyl, chloro, chloromethyl, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl, morpholinylmethyl and dimethylmorpholinylmethyl.

Typical substituents on $R^2$ include methyl, ethyl and n-propyl, especially methyl.

Representative values of $R^2$ include hydroxymethyl-cyclohexylmethyl, cyanobenzyl, hydroxymethyl-benzyl, pyrazolylmethyl, dimethyl-pyrazolylmethyl, methyl-isoxazolylmethyl, thiazolylmethyl, methyl-thiazolylmethyl, ethyl-thiazolylmethyl, methyl-thiazolylethyl, imidazolylmethyl, methyl-imidazolylmethyl, ethyl-imidazolylmethyl, benzyl-imidazolylmethyl, benzimidazolylmethyl, methyl-oxadiazolylmethyl, triazolylmethyl, methyl-triazolylmethyl, ethyl-triazolylmethyl, propyl-triazolylmethyl, benzyl-triazolylmethyl, pyridinylmethyl-triazolylmethyl, cyanomethyl-triazolylmethyl, dimethylaminomethyl-triazolylmethyl, aminoethyl-triazolylmethyl, dimethylaminoethyl-triazolylmethyl, dimethylaminocarbonylmethyl-triazolylmethyl, N-methylpiperidinyl-triazolylmethyl, pyrrolidinylethyl-triazolylmethyl, piperazinylethyl-triazolylmethyl, morpholinylethyl-triazolylmethyl, methyl-tetrazolylmethyl, pyridinylmethyl, methyl-pyridinylmethyl, dimethyl-pyridinylmethyl, ethoxy-pyridinylmethyl, cyclopropylmethoxy-pyridinylmethyl, pyridazinylmethyl, chloro-pyridazinylmethyl, pyrimidinylmethyl, pyrazinylmethyl, quinolinylmethyl, isoquinolinylmethyl and quinoxalinylmethyl.

Specific values of $R^2$ include methyl-triazolylmethyl, ethyl-triazolylmethyl, propyl-triazolylmethyl and pyridinyl-methyl. A favoured value of $R^2$ is methyl-triazolylmethyl.

A particular sub-class of compounds according to the invention is represented by the compounds of formula IIA, and salts and prodrugs thereof:

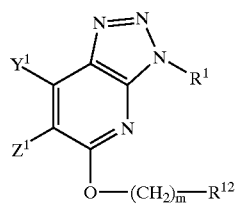

(IIA)

wherein $Y^1$ represents hydrogen or methyl;

$Z^1$ represents $C_{1-6}$ alkyl, $C_{3-7}$ cycloalkyl, $C_{4-7}$ cycloalkenyl, $C_{6-8}$ bicycloalkyl, aryl, $C_{3-7}$ heterocycloalkyl, heteroaryl, $C_{2-7}$ alkoxycarbonyl or di($C_{1-6}$)alkylamino, any of which groups may be optionally substituted;

$R^1$ is as defined with reference to formula I above;

m is 1 or 2, preferably 1; and $R^{12}$ represents aryl or heteroaryl, either of which groups may be optionally substituted.

Suitably, $Y^1$ represents hydrogen.

Examples of typical substituents on the group $Z^1$ include $C_{1-6}$ alkyl and halogen, typically methyl, fluoro or chloro, and especially fluoro.

Selected values for the group $Z^1$ include methyl, ethyl, isopropyl, tert-butyl, 1,1-dimethylpropyl, 2,2-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, fluorophenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino.

Illustrative values for the group $Z^1$ include methyl, ethyl, isopropyl, tert-butyl, 1,1-dimethylpropyl, 2,2-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino.

Representative values for the group $Z^1$ include methyl, ethyl, isopropyl, tert-butyl, 1,1-dimethylpropyl, methyl-cyclopropyl, cyclobutyl, methyl-cyclobutyl, cyclopentyl, methyl-cyclopentyl, cyclohexyl, cyclobutenyl, bicyclo[2.1.1]hex-1-yl, bicyclo[2.2.1]heptan-1-yl, phenyl, pyrrolidinyl, methyl-pyrrolidinyl, piperidinyl, morpholinyl, thiomorpholinyl, pyridinyl, furyl, thienyl, chloro-thienyl, methoxycarbonyl and diethylamino.

Specific values of $Z^1$ include tert-butyl, 2,2-dimethylpropyl, cyclobutyl, phenyl, 2-fluorophenyl, 3-fluorophenyl, 4-fluorophenyl, 2-furyl, 3-furyl, 2-thienyl, 3-thienyl and methoxycarbonyl. More particularly, $Z^1$ may represent tert-butyl, 2,2-dimethylpropyl, cyclobutyl, phenyl, 2-fluorophenyl, 3-fluorophenyl, 4-fluorophenyl, 2-furyl, 3-furyl, 2-thienyl or 3-thienyl.

Particular values for the group $Z^1$ include phenyl and methoxycarbonyl. In one embodiment, $Z^1$ represents 2,2-dimethylpropyl, cyclobutyl, phenyl, 2-thienyl, 3-thienyl or methoxycarbonyl. In another embodiment, $Z^1$ represents 2,2-dimethylpropyl, cyclobutyl, phenyl, 2-thienyl or 3-thienyl. In a further embodiment, $Z^1$ represents phenyl. In a still further embodiment, $Z^1$ represents methoxycarbonyl. In a yet further embodiment, $Z^1$ represents tert-butyl or cyclobutyl. In one more embodiment, $Z^1$ represents furyl.

A favoured value of $Z^1$ is cyclobutyl.

Suitably, $R^{12}$ represents phenyl, pyrazolyl, isoxazolyl, thiazolyl, imidazolyl, benzimidazolyl, oxadiazolyl, triazolyl, tetrazolyl, pyridinyl, pyridazinyl, pyrimidinyl, pyrazinyl, quinolinyl, isoquinolinyl or quinoxalinyl, any of which groups may be optionally substituted.

Selected values of $R^{12}$ include optionally substituted triazolyl and optionally substituted pyridinyl.

A particular value of $R^{12}$ is optionally substituted triazolyl.

Examples of typical substituents on the group $R^{12}$ include $C_{1-6}$ alkyl, aryl($C_{1-6}$)alkyl, pyridyl($C_{1-6}$)alkyl, halogen, cyano, cyano($C_{1-6}$)alkyl, hydroxymethyl, $C_{1-6}$ alkoxy, $C_{3-7}$ cycloalkyl($C_{1-6}$)alkoxy, di($C_{1-6}$)alkylamino($C_{1-6}$)alkyl, amino($C_{1-6}$)alkyl, di($C_{1-6}$)alkylaminocarbonyl($C_{1-6}$)alkyl, N-($C_{1-6}$)alkylpiperidinyl, pyrrolidinyl$_{(1-6)}$alkyl, piperazinyl ($C_{1-6}$)alkyl and morpholinyl($C_{1-6}$)alkyl.

Illustrative values of specific substituents on the group $R^{12}$ include methyl, ethyl, n-propyl, benzyl, pyridinylmethyl, chloro, cyano, cyanomethyl, hydroxymethyl, ethoxy, cyclopropylmethoxy, dimethylaminomethyl, aminoethyl, dimethylaminoethyl, dimethylaminocarbonylmethyl, N-methylpiperidinyl, pyrrolidinylethyl, piperazinylethyl and morpholinylmethyl.

Typical substituents on $R^{12}$ include methyl, ethyl and n-propyl, especially methyl.

Particular values of $R^{12}$ include cyanophenyl, hydroxymethyl-phenyl, pyrazolyl, dimethyl-pyrazolyl, methyl-isoxazolyl, thiazolyl, methyl-thiazolyl, ethyl-thiazolyl, imidazolyl, methyl-imidazolyl, ethyl-imidazolyl, benzyl-imidazolyl, benzimidazolyl, methyl-oxadiazolyl, triazolyl, methyl-triazolyl, ethyl-triazolyl, propyl-triazolyl, benzyl-triazolyl, pyridinylmethyl-triazolyl, cyanomethyl-triazolyl, dimethylaminomethyl-triazolyl, aminoethyl-triazolyl, dimethylaminoethyl-triazolyl, dimethylaminocarbonylmethyl-triazolyl, N-methylpiperidinyl-triazolyl, pyrrolidinylethyl-triazolyl, piperazinylethyl-triazolyl, morpholinylethyl-triazolyl, methyl-tetrazolyl, pyridinyl, methyl-pyridinyl, dimethyl-pyridinyl, ethoxy-pyridinyl, cyclopropylmethoxy-pyridinyl, pyridazinyl, chloro-pyridazinyl, pyrimidinyl, pyrazinyl, quinolinyl, isoquinolinyl and quinoxalinyl.

Specific values of $R^{12}$ include methyl-triazolyl, ethyl-triazolyl, propyl-triazolyl and pyridinyl. A favoured value of $R^{12}$ is methyl-triazolyl.

A particular subset of the compounds of formula IIA above is represented by the compounds of formula IIB, and pharmaceutically acceptable salts thereof:

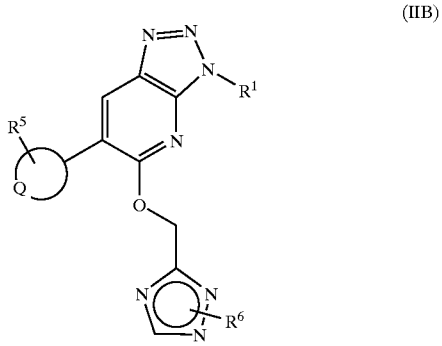

(IIB)

wherein
  $R^1$ is as defined with reference to formula I above;
  Q represents the residue of a cyclopropyl, cyclobutyl, cyclopentyl, cyclohexyl, phenyl, furyl or thienyl ring;
  $R^5$ represents hydrogen, methyl or fluoro; and
  $R^6$ represents hydrogen, methyl, ethyl or n-propyl.

The present invention also provides a compound of formula IIB as depicted above, or a pharmaceutically acceptable salt thereof, wherein
  Q represents the residue of a cyclopropyl, cyclobutyl, cyclopentyl, cyclohexyl, phenyl or thienyl ring;
  $R^6$ represents hydrogen or methyl; and
  $R^1$ and $R^5$ are as defined above.

The present invention further provides a compound of formula IIB as depicted above, or a pharmaceutically acceptable salt thereof, wherein
  Q represents the residue of a cyclopropyl, cyclobutyl, cyclopentyl, cyclohexyl or phenyl ring; and
  $R^1$, $R^5$ and $R^6$ are as defined above.

In relation to formula IIB above, $R^1$ suitably represents phenyl, fluorophenyl, difluorophenyl or (fluoro)(methoxy)phenyl. Particular values of $R^1$ include phenyl and fluorophenyl.

Suitably, Q represents the residue of a cyclobutyl, phenyl, furyl or thienyl ring. Particular rings of which Q is the residue include cyclobutyl, phenyl and thienyl.

In a favoured embodiment, Q suitably represents the residue of a cyclobutyl ring. In another embodiment, Q represents the residue of a phenyl ring. In a further embodiment, Q represents the residue of a 2-thienyl or 3-thienyl moiety. In a still further embodiment, Q represents the residue of a 2-furyl or 3-furyl moiety.

Suitably, $R^5$ represents hydrogen or fluoro, typically hydrogen.

Typically, $R^6$ represents methyl, ethyl or n-propyl. Suitably, $R^6$ represents methyl.

Another subset of the compounds of formula IIA above is represented by the compounds of formula IIC, and pharmaceutically acceptable salts thereof:

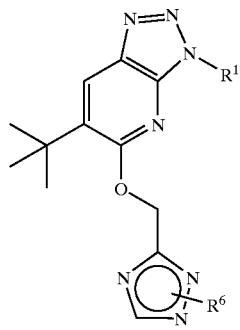

(IIC)

wherein
  $R^1$ is as defined with reference to formula I above; and
  $R^6$ is as defined with reference to formula IIB above.

Another sub-class of compounds according to the invention is represented by the compounds of formula IID, and salts and prodrugs thereof:

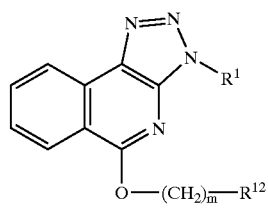

(IID)

wherein
  $R^1$ is as defined with reference to formula I above; and
  m and $R^{12}$ are as defined with reference to formula IIA above.

A particular subset of the compounds of formula IID above is represented by the compounds of formula IIE, and pharmaceutically acceptable salts thereof:

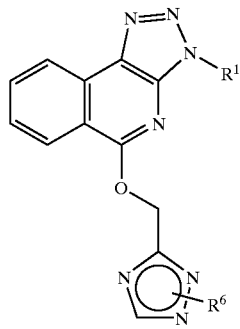

(IIE)

wherein
  $R^1$ is as defined with reference to formula I above; and
  $R^6$ is as defined with reference to formula IIB above.

Specific compounds within the scope of the present invention include:

3-phenyl-5-(2-methyl-2H-1,2,4-triazol-3-ylmethoxy)-6-methoxycarbonyl-1,2,3-triazolo[4,5-b]pyridine;

3,6-diphenyl-5-(2-methyl-2H-1,2,4-triazol-3-ylmethoxy)-1,2,3-triazolo[4,5-b]pyridine;
3-(2-fluorophenyl)-5-(2-methyl-2H-1,2,4-triazol-3-ylmethoxy)-6-phenyl-1,2,3-triazolo[4,5-b]pyridine;
3-(2-fluorophenyl)-5-(2-methyl-2H 1,2,4-triazol-3-ylmethoxy)-6-(thien-3-yl)-1,2,3-triazolo[4,5-b]pyridine;
3-(2-fluorophenyl)-5-(2-methyl-2H-1,2,4-triazol-3-ylmethoxy)-6-(thien-2-yl)-1,2,3-triazolo[4,5-b]pyridine;
3-(2-fluorophenyl)-5-(2-methyl-2H-1,2,4-triazol-3-ylmethoxy)-6-(2,2-dimethylpropyl)-1,2,3-triazolo[4,5-b]pyridine;
3-(2-fluorophenyl)-5-(2-methyl-2H-1,2,4-triazol-3-ylmethoxy)-6-cyclobutyl-1,2,3-triazolo[4,5-b]pyridine;
3-(2-fluorophenyl)-6-(2-fluorophenyl)-5-(2-methyl-2H-1,2,4-triazol-3-ylmethoxy)-1,2,3-triazolo[4,5-b]pyridine;
3-(2-fluorophenyl)-6-(3-fluorophenyl)-5-(2-methyl-2H-1,2,4-triazol-3-ylmethoxy)-1,2,3-triazolo[4,5-b]pyridine;
3-(2-fluorophenyl)-6-(4-fluorophenyl)-5-(2-methyl-2H-1,2,4-triazol-3-ylmethoxy)-1,2,3-triazolo[4,5-b]pyridine;
3-(2-fluorophenyl)-6-(2-furyl)-5-(2-methyl-2H-1,2,4-triazol-3-ylmethoxy)-1,2,3-triazolo[4,5-b]pyridine;
3-(2-fluorophenyl)-6-(3-furyl)-5-(2-methyl-2H-1,2,4-triazol-3-ylmethoxy)-1,2,3-triazolo[4,5-b]pyridine;
3-(2-fluorophenyl)-5-(1-methyl-1H-1,2,4-triazol-3-ylmethoxy)-6-(3-thienyl)-1,2,3-triazolo[4,5-b]pyridine;
3-(2-fluorophenyl)-5-(1-methyl-1H-1,2,4-triazol-3-ylmethoxy)-6-(2-thienyl)-1,2,3-triazolo[4,5-b]pyridine;
3-(2-fluorophenyl)-6-(3-fluorophenyl)-5-(1-methyl-1H-1,2,4-triazol-3-ylmethoxy)-1,2,3-triazolo[4,5-b]pyridine;
3-(2,6-difluorophenyl)-5-(2-methyl-2H-1,2,4-triazol-3-ylmethoxy)-6-(3-thienyl)-1,2,3-triazolo[4,5-b]pyridine;
3-(2,6-difluorophenyl)-6-(3-fluorophenyl)-5-(2-methyl-2H-1,2,4-triazol-3-ylmethoxy)-1,2,3-triazolo[4,5-b]pyridine;.
6-cyclobutyl-3-(2,6-difluorophenyl)-5-(2-methyl-2H-1,2,4-triazol-3-ylmethoxy)-1,2,3-triazolo[4,5-b]pyridine;
3-(2,6-difluorophenyl)-6-(3-furyl)-5-(2-methyl-2H-1,2,4-triazol-3-ylmethoxy)-1,2,3-triazolo[4,5-b]pyridine;
6-cyclobutyl-3-(2,6-difluorophenyl)-5-(1-methyl-1H-1,2,4-triazol-3-ylmethoxy)-1,2,3-triazolo[4,5-b]pyridine;
6-(1,1-dimethylethyl)-5-(2-methyl-2H-1,2,4-triazol-3-ylmethoxy)-3-phenyl-1,2,3-triazolo[4,5-b]pyridine;
6-(1,1-dimethylethyl)-5-(1-methyl-1H-1,2,4-triazol-3-ylmethoxy)-3-phenyl-1,2,3-triazolo[4,5-b]pyridine;
6-(1,1-dimethylethyl)-5-(2-ethyl-2H-1,2,4-triazol-3-ylmethoxy)-3-phenyl-1,2,3-triazolo[4,5-b]pyridine;
6-(1,1-dimethylethyl)-3-(2-fluorophenyl)-5-(2-methyl-2H-1,2,4-triazol-3-ylmethoxy)-1,2,3-triazolo[4,5-b]pyridine;
6-(1,1-dimethylethyl)-5-(2-ethyl-2H-1,2,4-triazol-3-ylmethoxy)-3-(2-fluorophenyl)-1,2,3-triazolo[4,5-b]pyridine;
6-(1,1-dimethylethyl)-3-(2-fluorophenyl)-5-(2-propyl-2H-1,2,4-triazol-3-ylmethoxy)-1,2,3-triazolo[4,5-b]pyridine;
6-(1,1-dimethylethyl)-3-(2-fluorophenyl)-5-(1-methyl-1H-1,2,4-triazol-3-ylmethoxy)-1,2,3-triazolo[4,5-b]pyridine;
3-(2,5-difluorophenyl)-6-(1,1-diethylethyl)-5-(2-methyl-2H-1,2,4-triazol-3-ylmethoxy)-1,2,3-triazolo[4,5-b]pyridine;
3-(2,5-difluorophenyl)-6-(1,1-dimethylethyl)-5-(2-ethyl-2H-1,2,4-triazol-3-ylmethoxy)-1,2,3-triazolo[4,5-b]pyridine;
3-(2,5-difluorophenyl)-6-(1,1-dimethylethyl)-5-(1-methyl-1H-1,2,4-triazol-3-ylmethoxy)-1,2,3-triazolo[4,5-b]pyridine;
3-(2,6-difluorophenyl)-6-(1,1-dimethylethyl)-5-(2-methyl-2H-1,2,4-triazol-3-ylmethoxy)-1,2,3-triazolo[4,5-b]pyridine;
6-(1,1-dimethylethyl)-3-(2-fluoro-6-methoxyphenyl)-5-(2-methyl-2H-1,2,4-triazol-3-ylmethoxy)-1,2,3-triazolo[4,5-b]pyridine;
5-(2-methyl-2H-1,2,4-triazol-3-ylmethoxy)-3-phenyl-1,2,3-triazolo[4,5-c]isoquinoline;
5-(2-ethyl-2H-1,2,4-triazol-3-ylmethoxy)-3-phenyl-1,2,3-triazolo[4,5-c]isoquinoline;
3-phenyl-5-(2-propyl-2H-1,2,4-triazol-3-ylmethoxy)-1,2,3-triazolo[4,5-c]isoquinoline;
5-(1-methyl-1H-1,2,4-triazol-3-ylmethoxy)-3-phenyl-1,2,3-triazolo[4,5-c]isoquinoline;
3-phenyl-5-(pyridin-2-ylmethoxy)-1,2,3-triazolo[4,5-c]isoquinoline;

and salts and prodrugs thereof.

Also provided by the present invention is a method for the treatment and/or prevention of anxiety which comprises administering to a patient in need of such treatment an effective amount of a compound of formula I as defined above or a pharmaceutically acceptable salt thereof or a prodrug thereof.

Further provided by the present invention is a method for the treatment and/or prevention of convulsions (e.g. in a patient suffering from epilepsy or a related disorder) which comprises administering to a patient in need of such treatment an effective amount of a compound of formula I as defined above or a pharmaceutically acceptable salt thereof or a prodrug thereof.

The binding affinity ($K_i$) of the compounds according to the present invention for the α3 subunit of the human $GABA_A$ receptor is conveniently as measured in the assay described hereinbelow. The α3 subunit binding affinity ($K_i$) of the compounds of the invention is ideally 10 nM or less, preferably 2 nM or less, and more preferably 1 nM or less.

The compounds according to the present invention will ideally elicit at least a 40%, preferably at least a 50%, and more preferably at least a 60%, potentiation of the GABA $EC_{20}$ response in stably transfected recombinant cell lines expressing the α3 subunit of the human $GABA_A$ receptor. Moreover, the compounds of the invention will ideally elicit at most a 30%, preferably at most a 20%, and more preferably at most a 10%, potentiation of the GABA $EC_{20}$ response in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as may be demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as may be confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

In order to elicit their behavioural effects, the compounds of the invention will ideally be brain-penetrant; in other words, these compounds will be capable of crossing the so-called "blood-brain barrier". Preferably, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to. provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I as defined above may be prepared by a process which comprises reacting a compound of formula III with a compound of formula IV:

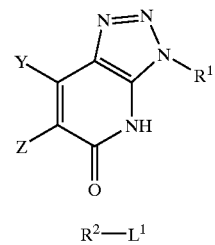

wherein Y, Z, $R^1$ and $R^2$ are as defined above, and $L^1$ represents a suitable leaving group.

The leaving group $L^1$ is typically a halogen atom, especially chloro.

The reaction between compounds III and IV is conveniently effected by stirring the reactants in a suitable solvent, in the presence of a base. Typically, the solvent is N,N-dimethylformamide, and the base is a strong base such as sodium hydride or lithium bis(trimethylsilyl)amide. In one preferred embodiment, the solvent is N,N-dimethylformamide or dimethylsulfoxide, and the base is caesium carbonate. In another preferred embodiment, the solvent is 1-methyl-2-pyrrolidinone, and the base is sodium hydroxide, in which case the reaction is advantageously performed at a temperature in the region of 0° C.

The intermediates of formula III above may be prepared by reacting a compound of formula V with a compound of formula VIA or VIB:

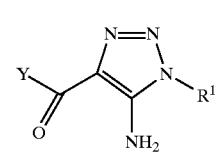

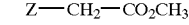

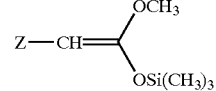

wherein Y, Z and $R^1$ are as defined above.

The reaction between compound V and compound VIA is conveniently effected under basic conditions in a suitable solvent, for example sodium methoxide in methanol.

The reaction between compound V and compound VIB is conveniently effected in the presence of a Lewis acid catalyst, e.g. boron trifluoride etherate, typically in an inert solvent such as dichloromethane at a temperature in the region of −78° C.

Under certain circumstances, for example depending upon the nature of the substituents Y, Z and $R^1$, the reaction between compound V and compound VIA or VIB may give rise to the uncyclized product of formula VIIA and/or VIIB:

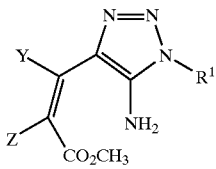

(VIIB)

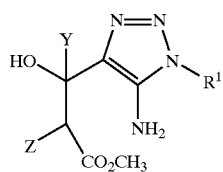

wherein Y, Z and R¹ are as defined above. It will generally be possible to convert compound VIIA and/or VIIB into the desired cyclized product of formula III by treatment with a strong base such a potassium bis(trimethylsilyl)amide, typically in an inert solvent such as toluene at an elevated temperature, e.g. a temperature in the region of 70° C.; or by treatment with potassium carbonate or caesium carbonate in a solvent such as methanol, typically at reflux.

In another procedure, the compounds of formula I as defined above may be prepared by a process which comprises reacting a compound of formula VIII with a compound of formula IX:

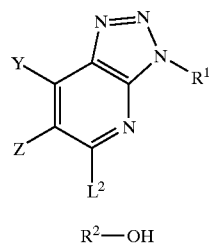

(VIII)

R²—OH (IX)

wherein Y, Z, R¹ and R² are as defined above, and $L^2$ represents a suitable leaving group.

The leaving group $L^2$ is suitably a halogen atom, typically chloro.

The reaction between compounds VIII and IX is conveniently effected by stirring the reactants in a suitable solvent, typically N,N-dimethylformamide, in the presence of a strong base such as sodium hydride.

In a further procedure, the compounds of formula I as defined above wherein Z represents alkyl, cycloalkyl, aryl or heteroaryl may be prepared by a process which comprises reacting a compound of formula X with a compound of formula XI:

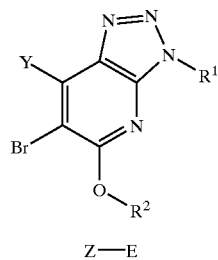

(X)

Z—E (XI)

wherein Y, Z, R¹ and R² are as defined above, and E represents the residue of an organometallic reagent, or E represents —B(OH)₂; in the presence of a transition metal catalyst.

Where Z represents alkyl or cycloalkyl, the moiety E suitably represents the residue of an organozinc reagent, in which case the intermediate XI is suitably prepared by reacting an alkyl or cycloalkyl halide, e.g. neopentyl iodide or cyclobutyl iodide, with zinc dust, typically in the presence of 1,2-dibromoethane and a solvent such as N,N-dimethylformamide. In this instance, the transition metal catalyst of use in the reaction betwen compounds X and XI is ideally tris(dibenzylideneacetone)dipalladium(0), and the reaction is conveniently effected in the presence of tri-2-furylphosphine and a solvent such as N,N-dimethylformamide.

Where Z represents aryl or heteroaryl, the moiety E suitably represents —Sn(Alk)₃ in which Alk represents $C_{1-6}$ alkyl, typically n-butyl. In this instance, the transition metal catalyst of use in the reaction between compounds X and XI is ideally tetrakis(triphenylphosphine)-palladium(0), and the reaction is conveniently effected in a solvent such as N,N-dimethylformamide, typically with heating, e.g. to a temperature in the region of 100° C.

Alternatively, where Z represents aryl or heteroaryl, the moiety E may suitably represent —B(OH)₂, in which case the transition metal catalyst of use in the reaction between compounds X and XI is ideally tetrakis(triphenylphosphine) palladium(0), and the reaction is conveniently effected in a solvent such as N,N-dimethylformamide, usually with heating, e.g. to a temperature in the region of 100° C., typically in the presence of caesium chloride.

The compounds of formula X above may suitably be prepared by reacting a compound of formula IV as defined above with a compound of formula XII:

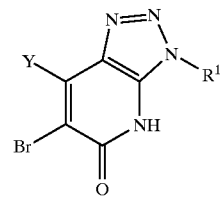

(XII)

wherein Y and R¹ are as defined above; under conditions analogous to those described above for the reaction between compounds III and IV.

The compounds of formula XII above may be prepared from the compounds of formula XIII:

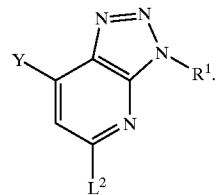

(XIII)

wherein Y, R¹ and $L^2$ are as defined above; by treatment with an alkali metal hydroxide, e.g. sodium hydroxide, followed by bromination which is typically effected by treatment with bromine, usually in the presence of glacial acetic acid.

The compounds of formula XIII above may be prepared from the compounds of formula XIV:

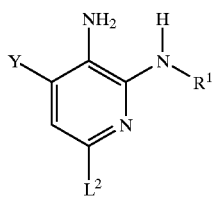

(XIV)

wherein Y, $R^1$ and $L^2$ are as defined above; by treatment with sodium nitrite.

The reaction is conveniently carried out by stirring the reagents at a temperature in the region of 0° C. in an aqueous mixture of glacial acetic acid and a mineral acid such as hydrochloric acid.

Similarly, the compounds in accordance with the present invention may be prepared by a process which comprises reacting sodium nitrite with a compound of formula XV:

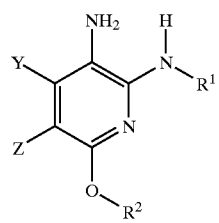

(XV)

wherein Y, Z, $R^1$ and $R^2$ are as defined above; under conditions analogous to those described above for the reaction betwen compound XIV and sodium nitrite.

The intermediates of formula XIV may be prepared by reacting a compound of formula XVI with a compound of formula XVII:

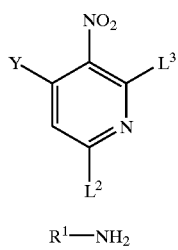

(XVI)

$R^1$—$NH_2$ (XVII)

wherein Y, $R^1$ and $L^2$ are as defined above, and $L^3$ represents a suitable leaving group; followed by reduction of the nitro group.

The leaving group $L^3$ is suitably a halogen atom, typically chloro.

The reaction between compounds XVI and XVII is conveniently effected in the presence of a base such as sodium hydrogen carbonate, suitably by heating the reactants in a solvent such as a lower alkanol, e.g. ethanol, typically at the reflux temperature of the solvent.

Reduction of the nitro group present in the compound thereby obtained is conveniently effected by catalytic hydrogenation.

In an alternative approach, the intermediates of formula III above may be prepared by reacting a compound of formula XVIII with a compound of formula XIX:

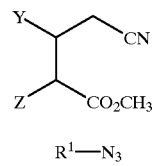

(XVIII)

$R^1$—$N_3$ (XIX)

wherein Y, Z and $R^1$ are as defined above.

The reaction is conveniently effected in a solvent such as tetrahydrofuran, in the presence of a strong base such as n-butyllithium.

Where they are not commercially available, the starting materials of formula IV, V, VIA, VIB, VIII, IX, XI, XV, XVI, XVII, XVIII and XIX may be prepared by methods analogous to those described in the accompanying Examples, or by standard methods well known from the art.

It will be understood that any compound of formula I initially obtained from any of the above processes may, where appropriate, subsequently be elaborated into a further compound of formula I by techniques known from the art. For example, a compound of formula I initially obtained wherein $R^2$ is unsubstituted may be converted into a corresponding compound wherein $R^2$ is substituted, typically by standard alkylation procedures, for example by treatment with a haloalkyl derivative in the presence of sodium hydride and N,N-dimethylformamide, or with a hydroxyalkyl derivative in the presence of triphenylphosphine and diethyl azodicarboxylate. Furthermore, a compound of formula I initially obtained wherein the $R^2$ substituent is substituted by a halogen atom, e.g. chloro, may be converted into the corresponding compound wherein the $R^2$ substituent is substituted by a di($C_{1-6}$)alkylamino moiety by treatment with the appropriate di($C_{1-6}$)alkylamine, typically with heating in a solvent such as 1,4-dioxane in a sealed tube.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk⁻ cells.
Reagents
Phosphate buffered saline (PBS).
Assay buffer: 10 mM KH$_2$PO$_4$, 100 mM KCl, pH 7.4 at room temperature.
[³H]-Flumazenil (18 nM for α1β3γ2 cells; 18 nM for α2β3γ2 cells; 10 nM for α3β3γ2 cells) in assay buffer.
flunitrazepam 100 μm in assay buffer.
Cells resuspended in assay buffer (1 tray to 10 ml).
Harvesting Cells Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.
Assay Can be carried out in deep 96-well plates or in tubes. Each tube contains:
300 μl of assay buffer.
50 μl of [³H]-flumazenil (final concentration for α1β3γ2: 1.8 nM; for α2β3γ2: 1.8 nM; for α3β3γ2: 1.0 nM).
50 μl of buffer or solvent carrier (e.g. 10% DMSO) if compounds are dissolved in 10% DMSO (total); test compound or flunitrazepam (to determine non-specific binding), 10 μM final concentration.
100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [³H]-flumazenil from the α2 and/or α3 subunit of the human GABA$_A$ receptor of 100 nM or less.

EXAMPLE 1

3-Phenyl-5-(2-methyl-2H-1,2,4-triazol-3-ylmethoxy)-6-methoxycarbonyl-1,2,3-triazolo[4,5-b]pyridine (a) 3-Phenyl-5-oxo-6-methoxycarbonyl-4H-1,2,3-triazolo[4,5-b]pyridine Dimethyl malonate (0.31 ml, 2.7 mmol) was added at room temperature to a stirred solution of sodium (0.065 g, 2.7 mmol) dissolved in dry methanol (8 ml) under nitrogen. A solution of 1-phenyl-4-formyl-5-amino-1,2,3-triazole (*Bull. Soc. Chim. Belg.,* 1988, 97, 85–86) (0.50 g, 2.66 mmol) in dry methanol (4 ml) was added and the mixture was stirred for 18 h. The white suspension was diluted with water (50 ml) and the solids were collected and dissolved in dichloromethane-methanol (2:1, 100 ml). The solution was washed with aqueous citric acid (1 M, 50 ml), dried (Na$_2$SO$_4$), filtered and concentrated to give 3-phenyl-5-oxo-6-methoxycarbonyl-4H-1,2,3-triazolo[4,5-b]pyridine (0.353 g, 49%) as a white powder. δ$_H$ (360 MHz; DMSO) 3.89 (3H, s), 7.56 (1H, t, J=7.5), 7.68 (2H, dd, J=7.5 and 7.5), 8.09 (2H, d, J=7.5), 8.92 (1H, s) and 12.67 (1H, br s); m/z (ES⁺) 271 (M+H⁺).

(b) 3-Phenyl-5-(2-methyl-2H-1,2,4-triazol-3-ylmethoxy)-6-methoxycarbonyl-1,2,3-triazolo[4,5-b]pyridine A mixture of 3-phenyl-5-oxo-6-methoxycarbonyl-4H-1,2,3-triazolo[4,5-b]pyridine (0.10 g, 0.37 mmol) and sodium hydride (55% in oil, 0.018 g, 0.40 mmol) in dry DMF (2 ml) was stirred at room temperature under nitrogen until all effervescence had ceased. A solution of 2-methyl-3-chloromethyl-1,2,4-triazole (0.065 g, 0.50 mmol) in dry DMF (0.5 ml) was added and the mixture was stirred for 4 days. Water was added and the aqueous solution was extracted with dichloromethane. The extracts were dried (Na$_2$SO$_4$), filtered and concentrated. Preparative thin-layer chromatography on silica gel, eluting with 5% methanol-dichloromethane, gave the alkylation product which was washed with hot ethyl acetate to give 3-phenyl-5-(2-methyl-2H-1,2,4-triazol-3-ylmethoxy)-6-methoxycarbonyl-1,2,3-triazolo[4,5-b]pyridine (0.036 g, 27%) as an off-white, crystalline solid, m.p. 188–190° C. Found: C, 55.97; H, 4.17; N, 26.93. C$_{17}$H$_{15}$N$_7$O$_3$ requires C, 55.89; H, 4.14; N, 26.84%. δ$_H$ (360 MHz; CDCl$_3$) 3.96 (3H, s), 4.08 (3H, s), 5.76 (2H, s), 7.50 (1H, t, J=7.5), 7.63 (2H, dd, J=7.5 and 7.5), 7.89 (1H, s), 8.23 (2H, d, J=7.5) and 8.96 (1H, s); m/z (ES⁺) 366 (M+H⁺).

EXAMPLE 2

3,6-Diphenyl-5-(2-methyl-2H-1,2,4-triazol-3-ylmethoxy)-1,2,3-triazolo[4 5-b]pyrdine (a) 3,6-Diphenyl-5-oxo-4H-1,2,3-triazolo[4,5-b]pyridine Methyl phenylacetate (0.39 ml, 2.7 mmol) was added at room temperature to a stirred solution of sodium (0.065 g, 2.7 mmol) dissolved in dry methanol (8 ml) under nitrogen, followed by addition of a solution of 1-phenyl-4-formyl-5-amino-1,2,3-triazole (*Bull. Soc. Chim. Belg.,* 1988, 97, 85–86) (0.50 g, 2.66 mmol) in dry methanol (4 ml). The orange solution was stirred at room temperature for 3.5 h, then refluxed for 1 h. Methanol was removed by evaporation and the residues were diluted with saturated aqueous ammonium chloride (50 ml). The yellow precipitate was collected and boiled in methanol. The resulting suspension was filtered and the yellow mother liquors were concentrated to give the crude aldol addition product as a yellow oil (0.375 g, 42%), m/z (ES⁺) 321 (M+H⁺). The crude material was dissolved in dry toluene (5 ml) under nitrogen and a solution of potassium hexamethyldisilazide (0.5 M in toluene, 2.2 ml) was added. The mixture was warmed to 70° C. for 1 h, then cooled and diluted with water (50 ml), acidified with aqueous citric acid (1 M) and extracted with ethyl acetate (100 ml). The extract was dried (Na$_2$SO$_4$), filtered and concentrated. Flash column chromatography on silica gel, eluting with 30% ethyl acetate-hexanes, gave the crude product, which was washed with diethyl ether to give 3,6-diphenyl-5-oxo-4H-1,2,3-triazolo[4,5b]pyridine (0.027 g, 9%) as a pink solid. δ$_H$ (360 MHz; CDCl$_3$) 7.45–7.50 (6H, m), 7.60 (2H, d, J=8), 7.87 (2H, d, J=7) and 8.24 (1H, s); m/z (ES⁺) 289 (M+H⁺).

(b) 3,6-Diphenyl-5-(2-methyl-2H-1,2,4-triazol-3-ylmethoxy)-1,2,3triazolo[4,5-b]pyridine A mixture of 3,6-diphenyl-5-oxo-4H-1,2,3-triazolo[4,5-b]pyridine (0.03 g, 0.10 mmol) and sodium hydride (55% in oil, 0.006 g, 0.12 mmol) in dry DMF (2 ml) was stirred at room temperature under nitrogen until all effervescence had ceased. A solution of 2-methyl-3-chloromethyl-1,2,4-triazole (0.025 g, 0.20 mmol) in dry DMF (0.5 ml) was added and the mixture was stirred for 4 days. Water (20 ml) was added and the aqueous solution was extracted with 10% methanol-dichloromethane (20 ml). The extract was dried ($Na_2SO_4$), filtered and concentrated. Preparative thin-layer chromatography on silica gel, eluting with 5% methanol-dichloromethane, gave the alkylation product which was recrystallised from ethyl acetate-hexane to give 3,6-diphenyl-5-(2-methyl-2H-1,2,4-triazol-3-ylmethoxy)-1,2,3-triazolo[4,5-b]pyridine (0.004 g, 10%) as a white, crystalline solid, m.p. 153–156° C. $\delta_H$ (360 MHz; $CDCl_3$) 3.71 (3H, s), 5.69 (2H, s), 7.42–7.54 (6H, m), 7.63 (2H, dd, J=8 and 8), 7.86 (1H, s), 8.24 (2H, d, J=8) and 8.32 (1H, s); m/z (ES+) 383 (M+H+).

EXAMPLE 3

3-(2-Fluorophenyl)-5-(2-methyl-2H-1,2,4-triazol-3-ylmethoxy)-6-phenyl-1,2,3-triazolo[4,5-b]pyridine a) 3-(2-Fluoronhenyl)-5-hyroxy-1,2,3-triazolo[4,5-b]pyridine A solution of 3-(2-fluorophenyl)-5-chloro-1,2,3-triazolo[4,5-b]pyridine (1.01 g, 4.06 mmol; prepared following the procedure described in GB Patent No. 1268772 but using 2-fluoroaniline instead of aniline) and 2M sodium hydroxide (4 ml) in DMSO (15 ml) was stirred at 100° C. under nitrogen for 3 h. The mixture was cooled, diluted with water (250 ml) and neutralised with aqueous citric acid. After standing for 18 h, the brown precipitate was collected, dissolved in dichloromethane (100 ml), dried ($Na_2SO_4$), filtered and concentrated to give 3-(2-fluorophenyl)-5-hydroxy-1,2,3-triazolo[4,5-b]pyridine (0.80 g, 86%) as a brown solid. $\delta_H$ (360 MHz; $d_6$-DMSO) 6.81 (1H, broad d, J=9), 7.50 (1H, dd, J=8 and 8), 7.60 (1H, dd, J=8 and 7), 7.68–7.72 (1H, m), 7.81 (1H, ddd, J=8, 8 and 2), 8.44 (1H, broad d, J=9) and 12.15 (1H, broad s); m/z (ES+) 231 (M+H+).

(b) 3-(2-Fluorophenyl)-5-hydroxy-6-bromo-1,2,3-triazolo[4,5-b]pyridine

Bromine (0.10 ml, 2 mmol) was added to a stirred solution of 3-(2-fluorophenyl)-5-hydroxy-1,2,3-triazolo[4,5-b]pyridine (0.23 g, 1.0 mmol) in glacial acetic acid (5 ml) at room temperature. After 4 h the solution was poured into water (150 ml). The precipitate was collected, dissolved in 10% methanol-dichloromethane (100 ml), dried ($Na_2SO_4$), filtered and concentrated to give 3-(2-fluorophenyl)-5-hydroxy-6-bromo-1,2,3-triazolo[4,5-b]pyridine (0.282 g, 91%) as a beige solid. $\delta_H$ (360 MHz; $CDCl_3$) 7.42–7.47 (2H, m), 7.60–7.71 (2H, m) and 8.48 (1H, s); m/z (ES+) 309, 311 (M+H+).

(c) 3-(2-Fluorophenyl-5-(2-methyl-2H-1,2,4-triazol-3-ylmethoxy)-6-bromo-1,2,3-triazolo[4,5-b]pyridine A mixture of 3-(2-fluorophenyl)-5-hydroxy-6-bromo-1,2,3-triazolo[4,5-b]pyridine (0.91 g, 2.94 mmol), 2-methyl-3-chloromethyl-1,2,4-triazole (0.46 g, 3.53 mmol) and caesium carbonate (1.40 g, 4.29 mmol) in dry DMF (15 ml) was stirred at room temperature under nitrogen for 18 h. The mixture was poured into water (150 ml) and extracted with ethyl acetate (2×100 ml). The extracts were dried ($Na_2SO_4$), filtered and concentrated. Flash column chromatography on silica gel, eluting with 4% methanol-dichloromethane, gave 3-(2-fluorophenyl)-5-(2-methyl-2H-1,2,4-triazol-3-ylmethoxy)-6-bromo-1,2,3-triazolo[4,5-b]pyridine (1.05 g, 88%) as a beige solid. $\delta_H$ (360 MHz; $CDCl_3$) 3.96 (3H, s), 5.59 (2H, s), 7.37–7.43 (2H, m), 7.56–7.64 (1H, m), 7.68 (1H, dd, J=7 and 7), 7.87 (1H, s) and 8.62 (1H, s); m/z (ES+) 404, 406 (M+H+).

(d) 3-(2-Fluorophenyl)-5-(2-methyl-2H-1,2,4-triazol-3-ylmethoxy)-6-phenyl-1,2,3-triazolo[4,5-b]pyridine A solution of 3-(2-fluorophenyl)-5-(2-methyl-2H-1,2,4-triazol-3-ylmethoxy)-6-bromo-1,2,3-triazolo[4,5-b]pyridine (0.15 g, 0.37 mmol), tributylphenyltin (0.14 ml, 0.44 mmol) and tetrakis(triphenylphosphine)-palladium(0) (0.02 g, 5 mol %) in dry DMF (2 ml) was purged with nitrogen and heated in a sealed tube at 100° C. for 24 h. The mixture was cooled, diluted with water (50 ml) and extracted with 10% methanol-dichloromethane (2×25 ml). The extracts were washed with brine (20 ml), dried ($Na_2SO_4$), filtered and concentrated. Flash column chromatography on silica gel, eluting with 2% methanol-dichloromethane, gave a yellow oil that solidified on trituration and washing with diethyl ether (2 ml). The material was recrystallised from ethyl acetate-hexane to give 3-(2-fluorophenyl)-5-(2-methyl-2H-1,2,4-triazol-3-ylmethoxy)-6-phenyl-1,2,3-triazolo[4,5-b]pyridine (0.077 g, 52%) as a cream-coloured solid, m.p. 144–146° C. (EtOAc-hexane). Found: C, 62.00; H, 4.00; N, 24.01. $C_{21}H_{16}N_7OF.0.33(H_2O)$ requires C, 61.91; H, 4.12; N, 24.07%. $\delta_H$ (360 MHz; $CDCl_3$) 3.64 (3H, s), 5.56 (2H, s), 7.38–7.47 (5H, m), 7.53 (2H, dd, J=8 and 1), 7.56–7.62 (1H, m), 7.71 (1H, dd, J=8 and 8), 7.82 (1H, s) and 8.32 (1H, s); m/z (ES+) 402 (M+H+).

EXAMPLE 4

3-(2-Fluorophenyl)-5-(2-methyl-2H-1,2,4-triazol-3-ylmethoxy)-6-(thien-3-yl)-1,2,3-triazolo[4,5-b]pyridine A mixture of 3-(2-fluorophenyl)-5-(2-methyl-2H-1,2,4-triazol-3-ylmethoxy)-6-bromo-1,2,3-triazolo[4,5-b]pyridine (0.10 g, 0.247 mmol) (Example 3, step c), 3-thiopheneboronic acid (0.080 g, 0.60 mmol), caesium carbonate (0.26 g, 0.80 mmol) and tetrakis(triphenylphosphine)-palladium(0) (0.03 g, 10 mol %) in DMF (4 ml) and water (1 ml) was purged with nitrogen, then heated in a sealed tube at 100° C. for 5 h. The solution was cooled, diluted with water (50 ml) and extracted with 10% methanol-dichloromethane (2×30 ml). The extracts were washed with brine (30 ml), dried ($Na_2SO_4$), filtered and concentrated. Flash column chromatography on silica gel, eluting with 4% methanol-dichloromethane, gave a brown gum that solidified on trituration with ethyl acetate. The material was recrystallised from ethyl acetate to give 3-(2-fluorophenyl)-5-(2-methyl-2H-1,2,4-triazol-3-ylmethoxy)-6-(thien-3-yl)-1,2,3-triazolo[4,5-b]pyridine (0.059 g, 59%) as a beige solid, m.p. 133–135° C. (EtOAc). Found: C, 55.31; H, 3.38. $C_{19}H_{14}N_7OFS$ requires C, 55.40; H, 3.55%. $\delta_H$ (360 MHz; $CDCl_3$) 3.73 (3H, s), 5.60 (2H, s), 7.36–7.46 (4H, m), 7.56–7.62 (1H, m), 7.66 (1H, dd, J=3 and 1), 7.71 (1H, dd, J=8 and 8), 7.86 (1H, s) and 8.46 (1H, s); m/z (ES+) 408 (M+H+).

EXAMPLE 5

3-(2-Fluorophenyl)-5-(2-methyl-2H-1,2,4-triazol-3-ylmethoxy)-6-(thien-2-yl)-1,2,3-triazolo[4,5-b]pyridine Prepared as for Example 4 using 2-thiopheneboronic acid in place of 3-thiopheneboronic acid to give 3-(2- fluorophenyl)-5-(2-methyl-2H-1,2,4-triazol-3-ylmethoxy)-6-(thien-2-yl)-1,2,3-triazolo[4,5-b]pyridine (0.048 g, 32%) as an off-white solid, m.p. 160–162° C. (EtOAc-hexane). Found: C, 5.74; H, 3.43; N, 23.73. $C_{19}H_{14}N_7OFS.0.1(H_2O)$ requires C, 55.77; H, 3.50; N, 23.96%. $\delta_H$ (360 MHz; $CDCl_3$) 3.83 (3H, s), 5.64 (2H, s), 7.12 (1H, d, J=5 and 4), 7.38–7.44 (3H, m), 7.52 (1H, d, J=5), 7.58–7.63 (1H, m), 7.71 (1H, dd, J=8 and 8), 7.88 (1H, s) and 8.58 (1H, s); m/z (ES+) 408 (M+H$^+$).

EXAMPLE 6

3-(2-Fluorophenyl)-5-(2-methyl-2H-1,2,4-triazol-3-ylmethoxy)-6-(2,2-dimethylpropyl)-1,2,3-triazolo[4,5-b]pyridine A suspension of acid washed zinc dust (0.12 g, 1.80 mmol) and 1,2-dibromoethane (0.015 ml, 10 mol %) in dry DMF (3 ml) was stirred at room temperature under nitrogen for 5 min then warmed to 40° C. A solution of neopentyl iodide (0.25 ml, 1.85 mmol) in dry DMF (1 ml) was added and the mixture was stirred at 40° C. for 3 h. A solution of 3-(2-fluorophenyl)-5-(2-methyl-2H-1,2,4-triazol-3-ylmethoxy)-6-bromo-1,2,3-triazolo[4,5-b]pyridine (0.15 g, 0.37 mmol) (Example 3, step c), tris(dibenzylideneacetone)dipalladium(0) (0.008 g, 2.5 mol %) and tri-2-furylphosphine (0.017 g, 20 mol %) in dry DMF (2 ml) was stirred at 40° C. under nitrogen for 10 min followed by addition of the organozinc reagent via syringe. The mixture was stirred for 18 h at 40° C. then cooled, diluted with water (60 ml), acidified with 1M aqueous citric acid and extracted with dichloromethane (2×30 ml). The extracts were dried ($Na_2SO_4$), filtered and concentrated. Preparative thin layer chromatography on silica gel, eluting with 2% methanol-dichloromethane, and trituration of the product with diethyl ether gave 3-(2-fluorophenyl)-5-(2-methyl-2H-1,2,4triazol-3-ylmethoxy)-6-(2,2-dimethylpropyl)-1,2,3-triazolo[4,5-b]pyridine (0.060 g, 41%) as a white solid, m.p. 130–133° C. Found: C, 60.03; H, 5.51; N, 24.37. $C_{20}H_{22}N_7OF.0.25(H_2O)$ requires C, 60.06; H, 5.67; N, 24.52%. $\delta_H$ (360 MHz; $CDCl_3$) 0.93 (9H, s), 2.68 (2H, s), 3.82 (3H, s),5.52 (2H, s), 7.36–7.42 (2H, m), 7.54–7.61 (1H, m), 7.69 (1H, dd, J=7 and 7), 7.86 (1H, s) and 8.10 (1H, s); m/z (ES+) 396 (M+H$^+$).

EXAMPLE 7

3-(2-Fluorophenyl)-5-(2-methyl-2H-1,2,4-triazol-3-ylmethoxy)-6-cyclobutyl-1,2,3-triazolo[4,5-b]pyridine Prepared as for Example 6 using cyclobutyl iodide in place of neopentyl iodide to give 3-(2-fluorophenyl)-5-(2-methyl-2H-1,2,4-triazol-3-ylmethoxy)-6-cyclobutyl-1,2,3-triazolo[4,5-b]pyridine (0.031 g, 11%) as a white solid, m.p. 120–122° C. (EtOAc-hexane). Found: C, 59.3; H, 4.6. $C_{19}H_{18}FN_7O.0.25(H_2O)$ requires C, 59.4; H, 4.9. $\delta_H$ (360 MHz; $CDCl_3$)1.85–2.20 (4H, m), 2.36–2.44 (2H, m), 3.71 (1H, quintuplet, J=8), 3.83 (3H, s), 5.52 (2H, s), 7.35–7.41 (2H, m), 7.50–7.59 (1H, m), 7.68 (1H, dd, J=7 and 7), 7.86 (1H, s) and 8.16 (1H, s); m/z (ES+) 380 (M+H$^+$).

EXAMPLE 8

3-(2-Fluorophenyl)-6-(2-fluorophenyl)-5-(2-methyl-2H-1,2,4-triazol-3-ylmethoxy)-1,2,3-triazolo[4,5-b]pyridine Prepared as for Example 4 using 2-fluorophenylboronic acid in place of 3-thiopheneboronic acid to give 3-(2-fluorophenyl)-6-(2-fluorophenyl)-5-(2-methyl-2H-1,2,4-triazol-3-ylmethoxy)-1,2,3-triazolo[4,5-b]pyridine (0.014 g, 13%) as an off-white solid. $\delta_H$ (400 MHz; $CDCl_3$) 3.69 (3H, s), 5.55 (2H, s), 7.15 (1H, dd, J=9 and 9), 7.24 (1H, dd, J=7 and 7), 7.37–7.44 (4H, m), 7.57–7.62 (1H, m), 7.73 (1H, ddd, J=8, 8 and 2), 7.80 (1H, s) and 8.31 (1H, s); m/z (ES+) 420 (M+H$^+$).

EXAMPLE 9

3-(2-Fluorophenyl)-6-(3-fluorophenyl)-5-(2-methyl-2H-1,2,4-triazol-3-ylmethoxy-1,2,3-triazolo[4,5-b]pyridine Prepared as for Example 4 using 3-fluorophenylboronic acid in place of 3-thiopheneboronic acid to give 3-(2-fluorophenyl)-6-(3-fluorophenyl)-5-(2-methyl-2H-1,2,4-triazol-3-ylmethoxy)-1,2,3-triazolo[4,5-b]pyridine (0.081 g, 52%) as an off-white solid, m.p. 143–145° C. ($Et_2O$). Found: C, 59.68; H, 3.59; N, 23.01. $C_{21}H_{15}F_2N_7O.0.25(H_2O)$ requires C, 59.50; H, 3.69; N, 23.13. $\delta_H$ (400 MHz; $CDCl_3$) 3.68 (3H, s), 5.57 (2H, s), 7.12 (1H, dd, J=9 and 9), 7.26–7.33 (2H, m), 7.38–7.45 (3H, m), 7.57–7.62 (1H, m), 7.70 (1H, dd, J=8 and 8), 7.83 (1H, s) and 8.33 (1H, s); m/z (ES+) 420 (M+H$^+$).

EXAMPLE 10

3-(2-Fluorophenyl)-6-(4-fluorophenyl)-5-(2-methyl-2H-1,2,4-triazol-3-ylmethoxy)-1,2,3-triazolo[4,5-b]pyridine Prepared as for Example 4 using 4-fluorophenylboronic acid in place of 3-thiopheneboronic acid to give 3-(2-fluorophenyl)-6-(4-fluorophenyl)-5-(2-methyl-2H-1,2,4-triazol-3-ylmethoxy)-1,2,3-triazolo[4,5-b]pyridine (0.054 g, 52%) as a white solid, m.p. 142–145° C. ($Et_2O$). Found: C, 59.64; H, 3.79. $C_{21}H_{15}F_2N_7O.0.25(H_2O)$ requires C, 59.50; H, 3.69. $\delta_H$ (400 MHz;

$CDCl_3$ 3.66 (3H, s), 5.55 (2H, s), 7.15 (2H, dd, J=9 and 9), 7.40–7.44 (2H, m), 7.50–7.54 (2H, m), 7.57–7.62 (1H, m), 7.70 (1H, dd, J=8 and 8), 7.83 (1H, s) and 8.30 (1H, s); m/z (ES+) 420 (M+H$^+$).

EXAMPLE 11

3-(2-Fluorophenyl)-6-(2-furyl)-5-(2-methyl-2H-1,2,4-triazol-3-ylmethoxy)-1,2,3-triazolo[4,5-b]pyridine A mixture of 3-(2-fluorophenyl)-5-(2-methyl-2H-1,2,4-triazol-3-ylmethoxy)-6-bromo-1,2,3-triazolo[4,5-b]pyridine (0.12 g, 0.29 7 mmol) (Example 3, step c), 2-tributylstannylfuran (0.19 ml, 0.60 mmol) and tetrakis(triphenylphosphine)palladium(0) (0.02 g, 5 mol %) in DMF (3 ml) was heated in a sealed tube at 100° C. for 7 h. The solution was cooled, diluted with water (40 ml) and extracted with 10% methanol-dichloromethane (2×20 ml). The extracts were dried ($Na_2SO_4$), filtered and concentrated. The residue was dissolved in ethyl acetate-dichloromethane and decolourised with charcoal (50 mg). The filtrate was concentrated to give 3-(2-fluorophenyl)-6-(2-furyl)-5-(2-methyl-2H-1,2,4-triazol-3-ylmethoxy)-1,2,3-triazolo[4,5-b]pyridine (0.086 g, 74%) as an off-white solid, m.p. 170–173° C. Found: C, 57.28; H, 3.67. $C_{19}H_{14}FN_7O_2.0.5(H_2O)$ requires C, 57.00; H, 3.78. $\delta_H$ (400 MHz; $CDCl_3$) 3.84 (3H, s), 5.66 (2H, s), 6.51 (1H, dd, J=3 and 2), 6.93 (1H, d, J=3), 7.37–7.43 (2H, m), 7.56–7.60 (2H, m), 7.71 (1H, dd, J=8 and 8), 7.90 (1H, s) and 8.80 (1H, s); m/z (ES+) 392 (M+H$^+$).

EXAMPLE 12

3-(2-Fluorophenyl)-6-(3-furyl)-5-(2-methyl-2H-1,2,4-triazol-3-ylmethoxy)-1,2,3-triazolo[4,5-b]pyridine Prepared as for Example 11 using 3-tributylstannylfuran in place of 2-tributylstannylfuran to give 3-(2-fluorophenyl)-6-(3-furyl)-5-(2-methyl-2H-1,2,4triazol-3-ylmethoxy )-1,2,3-triazolo[4,5-b]pyridine (0.06 6 g, 57%) as an off-white solid, m.p . 145–146° C. (Et$_2$O). $\delta_H$ (400 MHz; CDCl$_3$) 3.81 (3H, s),5.63 (2H, s), 6.83 (1H, s), 7.37–7.43 (2H, m), 7.51 (1H, s), 7.55–7.65 (1H, m), 7.71 (1H, dd, J=8 and 8), 7.89 (1H, s), 7.97 (1H, s) and 8.46 (1H, s); m/z (ES+) 392 (M+H$^+$).

EXAMPLE 13

3-(2-Fluorophenyl)-5-(1-methyl-1H-1,2,4-triazol-3-ylmethoxy)-6-(3-thienyl)-1,2,3-triazolo[4,5-b]pyridine (a) 3-(2-Fluorophenyl)-5-(1-methyl-1H-1,2,4-triazol-3-ylmethoxy)-6-bromo-1,2,3-triazolo[4,5-b]pyridine Prepared as for Example 3, step c using 1-methyl-3-chloromethyl-1,2,4-triazole in place of 2-methyl-3-chloromethyl-1,2,4-triazole to give 3-(2-fluorophenyl)-5-(1-methyl-1H-1,2,4-triazol-3-ylmethoxy)-6-bromo-1,2,3-triazolo[4,5-b]pyridine (0.085 g, 26%) as a pale yellow solid. $\delta_H$ (400 MHz; CDCl$_3$) 3.93 (3H, s), 5.52 (2H, s), 7.34–7.40 (2H, m), 7.52–7.56 (1H, m), 7.72 (1H, ddd, J=8, 8 and 2), 8.03 (1H, s) and 8.56 (1H, s); m/z (ES+) 406, 404 (M+H$^+$).

(b) 3-(2-Fluorophenyl)-5-(1-methyl-1H-1,2,4-triazol-3-ylmethoxy)-6-(3-thienyl)-1,2,3-triazolo[4,5-b]pyridine Prepared as for Example 4 using 3-(2-fluorophenyl)-5-(1-methyl-1H-1,2,4-triazol-3-ylmethoxy)-6-bromo-1,2,3-triazolo[4,5-b]pyridine in place of 3-(2-fluorophenyl)-5-(2-methyl-2H-1,2,4-triazol-3-ylmethoxy)-6-bromo-1,2,3-triazolo[4,5-b]pyridine to give 3-(2-fluorophenyl)-5-(1-methyl-1H-1,2,4-triazol-3-ylmethoxy)-6-(3-thienyl)-1,2,3-triazolo[4,5-b]pyridine (0.014 g, 35%) as a pale pink solid, m.p. 174–176° C. (EtOAc-Et$_2$O). $\delta_H$ (400 MHz; CDCl$_3$) 3.93 (3H, s), 5.58 (2H, s), 7.34–7.40 (3H, m), 7.50–7.56 (2H, m), 7.78 (1H, dd, J=8 and 8), 7.90 (1H, dd, J=2 and 1), 8.03 (1H, s) and 8.47 (1H, s); m/z (ES+) 408 (M+H$^+$).

EXAMPLE 14

3-(2-Fluorophenyl)-5-(1-methyl-1H-1,2,4-triazol-3-ylmethoxy)-6-(2-thienyl)-1,2,3-triazolo[4,5-b]pyridine Prepared as for Example 13, step b using 2-thopheneboronic acid in place of 3-thiopheneboronic acid to give 3-(2-fluorophenyl)-5-(1-methyl-1H-1,2,4-triazol-3-ylmethoxy)-6-(2-thienyl)-1,2,3-triazolo[4,5-b]pyridine (0.027 g, 58%) as a white solid, m.p. 179–181° C. (EtOAc-Et$_2$O). Found: C, 55.72; H, 3.31. C$_{19}$H$_{14}$FN$_7$OS requires C, 56.01; H, 3.46. $\delta_H$ (400 MHz; CDCl$_3$) 3.93 (3H, s), 5.60 (2H, s), 7.09 (1H, dd, J=5 and 4), 7.35–7.40 (3H, m), 7.50–7.58 (1H, m), 7.68 (1H, dd, J=4 and 1), 7.78 (1H, dd, J=8 and 8), 8.04 (1H, s) and 8.56 (1H, s); m/z (ES+) 408 (M+H$^+$).

EXAMPLE 15

3-(2-Fluorophenyl)-6-(3-fluorophenyl)-5-(1-methyl-1H-1,2,4-triazol-3-ylmethoxy)-1,2,3-triazolo[4,5-b]pyridine Prepared as for Example 13, step b using 3-fluorophenylboronic acid in place of 3-thiopheneboronic acid to give 3-(2-fluorophenyl)-6-(3-fluorophenyl)-5-(1-methyl-1H-1,2,4-triazol-3-ylmethoxy)-1,2,3-triazolo[4,5-b]pyridine (0.031 g, 39%) as white needles, m.p. 202–205° C. (MeOH). $\delta_H$ (400 MHz; CDCl$_3$) 3.90 (3H, s), 5.54 (2H, s), 7.02–7.10 (1H, m), 7.35–7.45 (5H, m), 7.52–7.58 (1H, m), 7.77 (1H, dd, J=8 and 8), 7.99 (1H, s) and 8.31 (1H, s); m/z (ES+) 419 (M+H$^+$).

EXAMPLE 16

3-(2,6-Difluorophenyl)-5-(2-methyl-2H-1,2,4-triazol-3-ylmethoxy)-6-(3-thienyl)-1,2,3-triazolo[4,5-b]pyridine (a) 3-(2,6-Difluorophenyl)-1,2,3-triazolo[4,5-b]pyridin-5-one Prepared as for Example 3, step a using 3-(2,6-difluorophenyl)-5-chloro-1,2,3-triazolo[4,5-b]pyridine in place of 3-(2-fluorophenyl)-5-chloro-1,2,3-triazolo[4,5-b]pyridine to give 3-(2,6-difluorophenyl)-1,2,3-triazolo[4,5-b]pyridin-5-one (3.45 g, 85%) as a pale pink solid. $\delta_H$ (360 MHz; d$_6$-DMSO) 6.83 (1H, d, J=9), 7.54 (2H, dd, J=8 and 8), 7.78–7.86 (1H, m), 8.46 (1H, d, J=9) and 12.28 (1H, s); m/z (ES+) 249 (M+H$^+$).

(b) 3-(2,6-Difluorophenyl -6-bromo-1,2,3-triazolo[4,5-b]pyridin-5-one

Prepared as for Example 3, step b using 3-(2,6-difluorophenyl)-1,2,3-triazolo[4,5-b]pyridin-5-one in place of 3-(2-fluorophenyl)-1,2,3-triazolo[4,5-b]pyridin-5-one to give 3-(2,6-difluorophenyl)-6-bromo-1,2,3-triazolo[4,5b]pyridin-5-one (3.52 g, 61%) as a tan coloured solid. $\delta_H$ (360 MHz; d$_6$-DMSO) 7.54 (2H, dd, J=8 and 8), 7.78–7.87 (1H, m), 8.93 (1H, s) and 13.45 (1H, s); m/z (ES+) 329, 327 (M+H$^+$).

(c) 3-(2,6-Difluorophenyl)-5-(2-methyl-2H-1,2,4-triazol-3-ylmethoxy)-6-bromo-1,2,3-triazolo[4,5-b]pyridine Prepared as for Example 3, step c using 3-(2,6-difluorophenyl)-6-bromo-1,2,3-triazolo[4,5-b]pyridin-5-one in place of 3-(2-fluorophenyl)-6-bromo-1,2,3-triazolo[4,5-b]pyridin-5-one to give 3-(2,6-difluorophenyl)-5-(2-methyl-2H-1,2,4-triazol-3-ylmethoxy)-6-bromo-1,2,3-triazolo[4,5-b]pyridine (1.09 g, 56%) as a brown solid. $\delta_H$ (360 MHz; CDCl$_3$) 3.96 (3H, s), 5.56 (2H, s), 7.22 (2H, dd, J=8 and 8), 7.59≅7.64 (1H, m), 7.86 (1H, s) and 8.63 (1H, s); m/z (ES+) 424, 422 (M+H$^+$).

(d) 3-(2,6-Difluorophenyl)-5-(2-methyl-2H-1,2,4-triazol-3-ylmethoxy)-6-(3-thienyl -1,2,3-triazolo[4,5-b]pyridine Prepared as for Example 4 using 3-(2,6-difluorophenyl)-5-(2-methyl-2H-1,2,4-triazol-3-ylmethoxy)-6-bromo-1,2,3-triazolo[4,5-b]pyridine in place of 3-(2-fluorophenyl)-5-(2-methyl-2H-1,2,4-triazol-3-ylmethoxy)-6-bromo-1,2,3-triazolo[4,5-b]pyridine to give 3-(2,6-difluorophenyl)-5-(2-methyl-2H-1,2,4-triazol-3-ylmethoxy)-6-(3-thienyl)-1,2,3-triazolo[4,5-b]pyridine (0.053 g, 26%) as a pink solid, m.p. 171–172° C. $\delta_H$ (360 MHz; CDCl$_3$) 3.73 (3H, s), 5.57 (2H, s), 7.23 (2H, dd, J=8 and 8), 7.40–7.41 (2H, m), 7.57–7.65 (2H, m), 7.85 (1H, s) and 8.47 (1H, s); m/z (ES+) 426 (M+H$^+$).

EXAMPLE 17

3-(2,6-Difluorophenyl)-6-(3-fluorophenyl)-5-(2-methyl-2H-1,2,4-triazol-3-ylmethoxy)-1,2,3-triazolo[4,5-b]pyridine Prepared as for Example 16, step d using 3-fluorophenylboronic acid in place of 3-thiopheneboronic acid to give 3-(2,6-difluorophenyl)-6-(3-fluorophenyl)-5-(2-methyl-2H-1,2,4-triazol-3-ylmethoxy)-1,2,3-triazolo[4,5-b]pyridine (0.027 g, 13%) as an off-white solid, m.p. 137–140° C. (MeOH). $\delta_H$ (400 MHz; CDCl$_3$) 3.67 (3H, s), 5.34 (2H, s), 7.12 (1H, ddd, J=8, 8 and 2), 7.22–7.32 (4H, m), 7.42 (1H, ddd, J=8, 8 and 8), 7.61–7.64 (1H, m), 7.82 (1H, s) and 8.34 (1H, s); m/z (ES+) 438 (M+H$^+$).

EXAMPLE 18

6-Cyclobutyl-3-(2,6-difluorophenyl)-5-(2-methyl-2H-1,2,4-triazol-3-ylmethoxy)-1,2,3-triazolo[4,5-b]pyridine Prepared as for Example 7 using 3-(2,6-difluorophenyl)-5-(2-methyl-2H-1,2,4-triazol-3-ylmethoxy)-6-bromo-1,2,3-triazolo[4,5-b]pyridine in place of 3-(2-fluorophenyl)-5-(2-methyl-2H-1,2,4-triazol-3-ylmethoxy)-6-bromo-1,2,3-triazolo[4,5-b]pyridine to give 6-cyclobutyl-3-(2,6-difluorophenyl)-5-(2-methyl-2H-1,2,4-triazol-3-ylmethoxy)-1,2,3-triazolo[4,5-b]pyridine (0.022 g, 15%) as a white solid, m.p. 140–144° C. (EtOH-H$_2$O). $\delta_H$ (360 MHz; CDCl$_3$) 1.80–1.90 (1H, m), 2.00–2.20 (3H, m), 2.35–2.45 (2H, m), 3.70 (1H, quintuplet, J=8), 3.83 (3H, s), 5.49 (2H, s), 7.20 (2H, dd, J=8 and 8), 7.55–7.60 (1H, m), 7.85 (1H, s) and 8.17 (1H, s); m/z (ES+) 398 (M+H$^+$).

EXAMPLE 19

3-(2,6-Difluorophenyl)-6-(3-furyl)-5-(2-methyl-2H-1,2,4-triazol-3-ylmethoxy)-1,2,3-triazolo[4,5-b]pyridine Prepared as for Example 12 using 3-(2,6-difluorophenyl)-5-(2-methyl-2H-1,2,4-triazol-3-ylmethoxy)-6-bromo-1,2,3-triazolo[4,5-b]pyridine in place of 3-(2-fluorophenyl)-5-(2-methyl-2H-1,2,4-triazol-3-ylmethoxy)-6-bromo-1,2,3-triazolo[4,5-b]pyridine to give 3-(2,6-difluorophenyl)-6-(3-furyl)-5-(2-methyl-2H-1,2,4-triazol-3-ylmethoxy)-1,2,3-triazolo[4,5-b]pyridine (0.039 g, 29%) as a cream-coloured solid, m.p. 166–169° C. (MeOH-CH$_2$Cl$_2$). $\delta_H$ (360 MHz; CDCl$_3$) 3.80 (3H, s), 5.60 (2H, s), 6.82–6.83 (1H, m), 7.23 (2H, dd, J=9 and 9), 7.51–7.52 (1H, m), 7.55–7.65 (1H, m), 7.88 (1H, s), 7.96 (1H, s) and 8.47 (1H, s); m/z (ES+) 410 (M+H$^+$).

EXAMPLE 20

6-Cyclobutyl-3-(2,6-difluorophenyl)-5-(1-methyl-1H-1,2,4-triazol-3-ylmethoxy)-1,2,3-triazolo[4,5-b]pyridine (a) 3-(2,6-Difluorophenyl)-5-(1-methyl-1H-1,2,4-triazol-3-ylmethoxy)-6-bromo-1,2,3-triazolo [4,5-b]pyridine Prepared as for Example 13, step a from 3-(2,6-difluorophenyl)-6-bromo-1,2,3-triazolo[4,5-b]pyridin-5-one (Example 16, step b) to give 3-(2,6-difluorophenyl)-5-(1-methyl-1H-1,2,4-triazol-3-ylmethoxy)-6-bromo-1,2,3-triazolo[4,5-b]pyridine as a beige powder (0.302 g, 24%). $\delta_H$ (400 MHz; CDCl$_3$) 3.92 (3H, s), 5.48 (2H, s), 7.19 (2H, dd, J=9 and 9), 7.53–7.59 (1H, m), 8.02 (1H, s) and 8.58 (1H, s); m/z (ES+) 422, 424 (M+H$^+$).

(b) 6-Cyclobutyl-3-(2,6-difluorophenyl)-5-(1-methyl-1H-1,2,4-triazol-3-ylmethoxy)-1,2,3-triazolo[4,5-b]pyridine Prepared as for Example 7 using 3-(2,6-difluorophenyl)-5-(1-methyl-1H-1,2,4-triazol-3-ylmethoxy)-6-bromo-1,2,3-triazolo[4,5-b]pyridine in place of 3-(2-fluorophenyl)-5-(2-methyl-2H-1,2,4-triazol-3-ylmethoxy)-6-bromo-1,2,3-triazolo[4,5-b]pyridine to give 6-cyclobutyl-3-(2,6-difluorophenyl)-5-(1-methyl-1H-1,2,4-triazol-3-ylmethoxy)-1,2,3-triazolo[4,5-b]pyridine (0.007 g, 5%). $\delta_H$ (400 MHz; CDCl$_3$) 1.80–1.88 (1H, m), 2.01–2.17 (3H, m), 2.35–2.42 (2H, m), 3.73 (1H, quintuplet, J =8), 3.92 (3H, s), 5.42 (2H, s), 7.17 (2H, dd, J=8 and 8), 7.52–7.58 (1H, m), 8.01 (1H, s) and 8.10 (1H, s); m/z (ES+) 398 (M+H$^+$).

EXAMPLE 21

6-(1,1-Dimethylethyl)-5-(2-methyl-2H-1,2,4-triazol-3-ylmethoxy)-3-phenyl-1,2,3-triazolo[4,5-b]pyridine (a) 2-[α-(5-Amino-1-phenyl-1H-1,2,3-triazol-4-yl)-α-hydroxymethyl]-3,3-dimethylbutyric acid methyl ester A solution of 5-amino-4-formyl-1-phenyl-1H-1,2,3-triazole (prepared from phenyl azide and methyl cyanoacetate according to Bull. Chim. Soc. Belg., 1988, 97, 85–86) (0.20 g, 1.06 mmol) in dry dichloromethane (5 ml) was stirred at –78° C. under nitrogen. Boron trifluoride etherate (0.28 ml, 2.2 mmol) was added, followed by a solution of tert-butylketene methyl trimethylsilyl acetal (J. Org. Chem., 1991, 56, 4737–4741) (0.30 g, 1.5 mmol) in dry dichloromethane (1 ml). After stirring at –78° C. for 1 h the yellow solution was poured into water (25 ml) and extracted with dichloromethane (2×25 ml). The extracts were washed with brine (25 ml), dried (Na$_2$SO$_4$), filtered and concentrated. Flash column chromatography on silica, eluting with 20% then 40% then 50% ethyl acetate-hexane, gave 2-[α-(5-amino-1-phenyl-1H-1,2,3-triazol-4-yl)-α-hydroxymethyl]-3,3-dimethylbutyric acid methyl ester (0.25 g, 75%) as a white wax (1:1 mixture of diastereoisomers). $\delta_H$ (360 MHz; CDCl$_3$) 1.15 and 1.17 (9H, 2xs), 2.70 and 2.98 (1H, 2xd, J=7 and J=9), 3.54 and 3.71 (3H, 2xs), 4.09–4.30 (2H, 2xm), 5.15–5.29 (1H, 2xm) and 7.46 (5H, m); m/z (ES+) 319 (M+H$^+$).

(b) 3-Phenyl-6-(tert-butyl)-3,4-dihydro-1,2,3-triazolo[4,5-b]pyridin-5-one

A mixture of 2-[α-(5-amino-1-phenyl-1H-1,2,3-triazol-4-yl)-α-hydroxymethyl]-3,3-dimethylbutyric acid methyl ester (0.13 g, 0.41 mmol) and potassium carbonate (0.20 g, 1.45 mmol) in dry methanol (5 ml) was stirred at r.t. under nitrogen for 24 h then refluxed for 4 h. The mixture was cooled, diluted with water (20 ml), neutralised with 1M hydrochloric acid and extracted with dichloromethane (2×20 ml). The extracts were dried (Na$_2$SO$_4$), filtered and concentrated. Flash column chromatography on silica, eluting with 20% ethyl acetate-hexane, gave 3-phenyl-6-(tert-butyl)-3,4-dihydro-1,2,3-triazolo[4,5-b]pyridin-5-one (0.028 g, 25%) as a white powder. $\delta_H$ (360 MHz; CDCl$_3$) 1.34 (9H, s), 7.51 (1H, t, J=7), 7.59 (2H, dd, J=7 and 7), 7.77 (2H, d, J=7) and 8.06 (1H, s); m/z (ES+) 269 (M+H$^+$).

(c) 6-(1,1-Dimethylethyl)-5-(2-methyl-2H-1,2,4-triazol-3-ylmethoxy)-3-phenyl-1,2,3-triazolo[4,5-b]pyridine A mixture of 3-phenyl-6-(tert-butyl)-3,4-dihydro-1,2,3-triazolo[4,5-b]pyridin-5-one (0.025 g, 0.093 g), 2-methyl-3-chloromethyl-1,2,4-triazole hydrochloride (0.15 g, 1.1 mmol) and cesium carbonate (0.65 g, 2.0 mmol) in dry DMF (4 ml) was stirred at r.t. for 20 h. The mixture was diluted with water (50 ml) and 1M citric acid (5 ml), and extracted with dichloromethane (2×25 ml). The extracts were dried (Na$_2$SO$_4$), filtered and concentrated. Preparative thin-layer chromatography, eluting with 5% methanol-dichloromethane, gave 6-(1,1-dimethylethyl)-5-(2-methyl-2H-1,2,4-triazol-3-ylmethoxy)-3-phenyl-1,2,3-triazolo[4,5-b]pyridine (0.028 g, 83%) as a white solid, m.p. 165–167° C. δ$_H$ (360 MHz; CDCl$_3$) 1.43 (9H, s), 3.94 (3H, s), 5.69 (2H, s), 7.46 (1H, t, J=7), 7.60 (2H, dd, J=7 and 7), 7.93 (1H, s), 8.20 (2H, d, J=7) and 8.31 (1H, s); m/z (ES+) 364 (M+H$^+$).

EXAMPLE 22

6-(1,1-Dimethylethyl)-5-(1-methyl-1H-1,2,4-triazol-3-ylmethoxy)-3-phenyl-1,2,3-triazolo[4,5-b]pyridine Prepared as for Example 21, step c using 1-methyl-3-chloromethyl-1,2,4-triazole in place of 2-methyl-3-chloromethyl-1,2,4-triazole to give 6-(1,1-dimethylethyl)-5-(1-methyl-1H-1,2,4-triazol-3-ylmethoxy)-3-phenyl-1,2,3-triazolo[4,5-b]pyridine (0.043 g, 63%) as a white powder, m.p. 179–180° C. (MeOH-CH$_2$Cl$_2$). Found: C, 61.91; H, 5.73; N, 26.24. C$_{19}$H$_{21}$N$_7$O.0.33(H$_2$O) requires C, 61.77; H, 5.91; N, 26.54%. δ$_H$ (400 MHz; CDCl$_3$) 1.46 (9H, s), 3.94 (3H, s), 5.64 (2H, s), 7.42 (1H, t, J=8), 7.58 (2H, dd, J=8 and 8), 8.05 (1H, s), 8.24 (1H, s) and 8.36 (2H, d, J=8); m/z (ES+) 364 (M+H$^+$).

EXAMPLE 23

6-(1,1-Dimethylethyl)-5-(2-ethyl-2H-1,2,4-triazol-3-ylmethoxy)-3-phenyl-1,2,3-triazolo[4,5-b]pyridine Prepared as for Example 21, step c using 2-ethyl-3-chloromethyl-1,2,4-triazole in place of 2-methyl-3-chloromethyl-1,2,4-triazole to give 6-(1,1-dimethylethyl)-5-(2-ethyl-2H-1,2,4-triazol-3-ylmethoxy)-3-phenyl-1,2,3-triazolo[4,5-b]pyridine (0.056 g, 80%) as a white powder, m.p. 161–163° C. (MeOH-CH$_2$Cl$_2$). δ$_H$ (400 MHz; CDCl$_3$) 1.43 (3H, s), 1.46 (3H, t, J=7), 4.26 (2H, q, J=7), 5.70 (2H, s), 7.45 (1H, t, J=8), 7.58 (2H, dd, J=8 and 8), 7.95 (1H, s), 8.22 (2H, d, J =8) and 8.31 (1H, s); m/z (ES+) 364 (M+H$^+$).

EXAMPLE 24

6-(1,1-Dimethylethyl)-3-(2-fluorophenyl)-5-(2-methyl-2H-1,2,4-triazol-3-ylmethoxy)-1,2,3-triazolo[4,5-b]pyridine (a) 2-[α-(5-Amino-1-(2-fluorophenyl)-1H-1,2,3,triazol-4-yl)-α-hydroxymethyl]-3,3-dimethylbutyric acid methyl ester Prepared from 5-amino-1-(2-fluorophenyl)-4-formyl-1H-1,2,3-triazole (prepared from 2-fluorophenyl azide and methyl cyanoacetate according to *Bull. Chim. Soc. Belg.*, 1988, 97, 85–86) following the procedure in Example 21, step a to give 2-[α-(5-amino-1-(2-fluorophenyl)-1H-1,2,3-triazol-4-yl)-α-hydroxymethyl]-3,3-dimethylbutyric acid methyl ester (2.28 g, 70%) (3:1 mixture of diastereoisomers). Flash column chromatography on silica gel gave the pure major isomer as a white solid (1.29 g). δ$_H$ (400 MHz; CDCl$_3$) 1.15 (9H, s), 2.64 (1H, d, J=7), 2.96 (1H,d, J=9), 3.53 (3H, s), 4.02 (2H, s), 5.16 (1H, dd, J=9 and 7), 7.26–7.35 (2H, m) and 7.51–7.56 (2H, m); m/z (ES+) 337 (M+H$^+$).

(b) 3-(2-Fluorophenyl)-6-(tert-butyl)-3,4-dihydro-1,2,3-triazolo[4,5-b]pyridin-5-one Prepared as for Example 21, step b to give 3-(2-fluorophenyl)-6-(tert-butyl)-3,4-dihydro-1,2,3-triazolo[4,5-b]pyridin-5-one (0.40 g, 20%) as a pinkish solid. δ$_H$ (400 MHz; CDCl$_3$) 1.23 (9H, s), 7.35–7.41 (2H, m), 7.55–7.60 (1H, m), 7.68 (1H, dd, J=8 and 8), 7.98 (1H, s) and 12.00 (1H, s); m/z (ES+) 286 (M+H$^+$).

(c) 6-(1,1-Dimethylethyl -3-(2-fluorophenyl)-5-(2-methyl-2H-1,2,4-triazol-3-ylmethoxy)-1,2,3-triazolo[4,5-b]pyridine Prepared as for Example 21, step c to give 6-(1,1-dimethylethyl)-3-(2-fluorophenyl)-5-(2-methyl-2H-1,2,4-triazol-3-ylmethoxy)-1,2,3-triazolo[4,5-b]pyridine (0.068 g, 51%) as an off-white solid, m.p. 115–117° C. (Et$_2$O). Found: C, 59.40; H, 5.17; N, 25.15. C$_{19}$H$_{20}$N$_7$OF.0.25(H$_2$O) requires C, 59.13; H, 5.35; N, 25.41%. δ$_H$ (400 MHz; CDCl$_3$) 1.43 (9H, s), 3.81 (3H, s), 5.58 (2H, s), 7.35–7.40 (2H, m), 7.52–7.60 (1H, m), 7.65 (1H, dd, J=8 and 8), 7.81 (1H, s) and 8.30 (1H, s); m/z (ES+) 382 (M+H$^+$).

EXAMPLE 25

6-(1,1-Dimethylethyl)-5-(2-ethyl-2H-1,2,4-triazol-3-ylmethoxy -3-(2-fluorophenyl)-1,2,3-triazolo[4,5-b]pyridine Prepared as for Example 24, step c using 2-ethyl-3-chloromethyl-1,2,4-triazole in place of 2-methyl-3-chloromethyl-1,2,4-triazole to give 6-(1,1-dimethylethyl)-5-(2-ethyl-2H-1,2,4-triazol-3-ylmethoxy)-3-(2-fluorophenyl)-1,2,3-triazolo[4,5-b]pyridine (0.067 g, 48%) as an off-white solid, m.p. 117–120° C. (Et$_2$O). Found: C, 60.60; H, 5.59; N, 24.78. C$_{20}$H$_{22}$N$_7$OF requires C, 60.75; H, 5.61; N, 24.79%. δ$_H$ (400 MHz; CDCl$_3$) 1.38 (3H, t, J=7), 1.42 (9H, s), 4.16 (2H, q, J=7), 5.59 (2H, s), 7.35–7.41 (2H, m), 7.50–7.60 (1H, m), 7.69 (1H, dd, J=8 and 8), 7.90 (1H, s) and 8.30 (1H, s); m/z (ES+) 396 (M+H$^+$).

EXAMPLE 26

6-(1,1-Dimethylethyl)-3-(2-fluorophenyl)-5-(2-propyl-2H-1,2,4-triazol-3-ylmethoxy)-1,2,3-triazolo[4,5-b]pyridine Prepared as for Example 24, step c using 2-propyl-3-chloromethyl-1,2,4-triazole in place of 2-methyl-3-chloromethyl-1,2,4-triazole to give 6-(1,1-dimethylethyl)-3-(2-fluorophenyl)-5-(2-propyl-2H-1,2,4-triazol-3-ylmethoxy)-1,2,3-triazolo[4,5-b]pyridine (0.060 g, 42%) as colourless cubes, m.p. 127–129° C. (EtOAc-hexane). Found: C, 61.09; H, 5.86; N, 23.84. C$_{21}$H$_{24}$N$_7$OF. 0.2(H$_2$O) requires C, 61.06; H, 5.95; N, 23.74%. δ$_H$ (400 MHz; CDCl$_3$) 0.84 (3H, t, J=7), 1.42 (9H, s), 1.82 (2H, td, J=7 and 7), 4.06 (2H, t, J=7), 5.58 (2H, s), 7.38–7.42 (2H, m), 7.52–7.60 (1H, m), 7.69 (1H, dd, J=8 and 8), 7.90 (1H, s) and 8.30 (1H, s); m/z (ES+) 410 (M+H$^+$).

EXAMPLE 27

6-(1,1-Dimethylethyl)-3-(2-fluorophenyl)-5-(1-methyl-1H-1,2,4-triazol-3-ylmethoxy)-1,2,3-triazolo[4,5-b]pyridine Prepared as for Example 24, step c using 1-methyl-3-chloromethyl-1,2,4-triazole in place of 2-methyl-3-chloromethyl-1,2,4-triazole to give 6-(1,1-dimethylethyl)-3-(2-fluorophenyl)-5-(1-methyl-1H-1,2,4-triazol-3-ylmethoxy)-1,2,3-triazolo[4,5-b]pyridine (0.095 g, 71%) as an off-white solid, m.p. 127–129° C. (Et$_2$O). Found: C, 59.42; H, 5.28; N, 25.36. C$_{19}$H$_{20}$N$_7$OF.0.2(H$_2$O) requires C, 59.27; H, 5.34; N, 25.47%. δ$_H$ (400 MHz; CDCl$_3$) 1.44 (9H, s), 3.93 (1H, s), 5.51 (2H, s), 7.30–7.38 (2H, m), 7.50–7.55 (1H, m), 7.75 (1H, dd, J=8 and 8), 8.03 (1H, s) and 8.25 (1H, s); m/z (ES+) 382 (M+H$^+$).

EXAMPLE 28

3-(2,5-Difluorophenyl)-6-(1,1-dimethylethyl)-5-(2-methyl-2H-1,2,4-triazol-3-ylmethoxy)-1,2,3-triazolo[4,5-b]pyridine (a) 2-[α-(5-Amino-1-(2,5-difluorophenyl)-1H-1,2,3-triazol-4yl)-α-hydroxymethyl]-3,3-dimethylbutyric acid methyl ester Prepared from 5-amino-1-(2,5-difluorophenyl)-4-formyl-1H-1,2,3-triazole (prepared from 2,5-difluorophenyl azide and methyl cyanoacetate according to *Bull. Chim. Soc. Belg.*, 1988, 97, 85–86) following the procedure in Example 21, step a to give 2-[α-(5-amino-1-(2,5-difluorophenyl)-1H-1,2,3-triazol-4-yl)-α-hydroxymethyl]-3,3-dimethylbutyric acid methyl ester (2.09 g, 56%) (4:1 mixture of diastereoisomers). Data for major isomer: $\delta_H$ (360 MHz; CDCl$_3$) 1.15 (9H, s), 2.67 (1H, d, J=7), 2.96 (1H, d, J=9), 3.53 (3H, s), 4.08 (2H, s), 5.17 (1H, dd, J=9 and 7) and 7.23–7.32 (3H, m); m/z (ES+) 355 (M+H$^+$).

(b) 3-(2 5-Difluorophenyl)-6-(tert-butyl)-3,4-dihydro-1,2,3-triazolo[4,5-b]pyridin-5-one Prepared as for Example 21, step b using cesium carbonate in place of potassium carbonate to give 3-(2,5-difluorophenyl)-6-(tert-butyl)-3,4-dihydro-1,2,3-triazolo[4,5-b]pyridin-5-one (0.70 g, 39%) as a yellow solid. $\delta_H$ (400 MHz; CDCl$_3$) 1.27 (9H, s), 7.25–7.30 (1H, m), 7.32–7.40 (1H, m), 7.52–7.60 (1H, m), 8.01 (1H, s) and 11.50 (1H, s); m/z (ES+) 305 (M+H$^+$).

(c) 3-(2,5-Difluorophenyl)-6-(1,1-dimethylethyl)-5-(2-methyl-2H-1,2,4-triazol-3-ylmethoxy)-1,2,3-triazolo[4,5-b]pyridine Prepared as for Example 21, step c to give 3-(2,5-difluorophenyl)-6-(1,1-dimethylethyl)-5-(2-methyl-2H-1,2,4-triazol-3-ylmethoxy)-1,2,3-triazolo[4,5-b]pyridine (0.015 g, 19%) as an off-white solid. $\delta_H$ (400 MHz; CDCl$_3$) 1.43 (9H, s), 3.88 (3H, s), 5.60 (2H, s), 7.20–7.30 (1H, m), 7.32–7.38 (1H, m), 7.45–7.50 (1H, m), 7.89 (1H, s) and 8.31 (1H, s); m/z (ES+) 400 (M+H$^+$).

EXAMPLE 29

3-(2,5-Difluorophenyl)-6-(1,1-dimethylethyl)-5-(2-ethyl-2H-1,2,4-triazol-3-ylmethoxy)-1,2,3-triazolo[4,5-b]pyridine Prepared as for Example 28, step c using 2-ethyl-3-chloromethyl-1,2,4triazole in place of 2-methyl-3-chloromethyl-1,2,4triazole to give 3-(2,5-difluorophenyl)-6-(1,1-dimethylethyl)-5-(2-ethyl-2H-1,2,4-triazol-3-ylmethoxy)-1,2,3-triazolo[4,5-b]pyridine (0.064 g, 47%) as an off-white solid, m.p. 148–150° C. (Et$_2$O). Found: C, 57.06; H, 5.09; N, 23.32. C$_{20}$H$_{21}$N$_7$OF$_2$.0.33(H$_2$O) requires C, 57.28; H, 5.21; N, 23.38%. $\delta_H$ (360 MHz; CDCl$_3$) 1.42 (3H, t, J=7), 1.42 (9H, s), 4.21 (2H, q, J=7), 5.61 (2H, s), 7.20–7.430 (1H, m), 7.30–7.40 (1H, m), 7.45–7.52 (1H, m), 7.92 (1H, s) and 8.30 (1H, s); m/z (ES+) 414 (M+H$^+$).

EXAMPLE 30

3-(2.5-Difluorophenyl)-6-(1,1-dimethylethyl)-5-(1-methyl-1H-1,2,4-triazol-3-ylmethoxy)-1,2,3-triazolo[4,5-b]pyridine Prepared as for Example 28, step c using 1-methyl-3-chloromethyl-1,2,4-triazole in place of 2-methyl-3-chloromethyl-1,2,4-triazole to give 3-(2,5-difluorophenyl)-6-(1,1-dimethylethyl)-5-(1-methyl-1H-1,2,4-triazol-3-ylmethoxy)-1,2,3-triazolo[4,5-b]pyridine (0.10 g, 76%) as an off-white solid, m.p. 154–157° C/ (Et$_2$O). Found: C, 56.14; H, 4.80; N, 24.09. C$_{19}$H$_{29}$N$_7$OF$_2$.0.33(H$_2$O) requires C, 56.30; H, 4.89; N, 24.19%. $\delta_H$ (360 MHz; CDCl$_3$) 1.45 (9H, s), 3.93 (1H, s), 5.54 (2H, s), 7.15–7.25 (1H, m), 7.30–7.38 (1H, m), 7.52–7.60 (1H, m), 8.03 (1H, s) and 8.25 (1H, s); m/z (ES+) 400 (M+H$^+$).

EXAMPLE 31

3-(2,6-Difluorophenyl)-6-(1,1-dimethylethyl)-5-(2-methyl-2H-1,2,4-triazol-3-ylmethoxy)-1,2,3-triazolo[4,5-b]pyridine (a) 2-[α-(5-Amino-1-(2,6-difluorophenyl)-1H-1,2,3-triazol-4-yl)-α-hydroxymethyl]-3,3-dimethylbutyric acid methyl ester Prepared from 5-amino-1-(2,6-difluorophenyl)-4-formyl-1H-1,2,3-triazole prepared from 2,6-difluorophenyl azide and ethyl cyanoacetate according to *Bull. Chim. Soc. Belg.*, 1988, 97, 85–86) following the procedure in Example 21, step a to give 2-[α-(5-amino-1-(2,6-difluorophenyl)-1H-1,2,3-triazol-4-yl)-α-hydroxymethyl]-3,3-dimethylbutyric acid methyl ester (1.65 g, 68%) (5:1 mixture of diastereoisomers). Data for major isomer: $\delta_H$ (400 MHz; CDCl$_3$) 1.15 (9H, s), 2.68 (1H, d, J=7), 2.96 (1H, d, J=9), 3.52 (3H, s), 3.95 (2H, s), 5.17 (1H, dd, J=9 and 7), 7.14 (2H, dd, J=8 and 8) and 7.53 (1H, tt, J=8 and 4); m/z (ES+) 355 (M+H$^+$).

(b) 3-(2,6-Difluorophenyl)-6-(tert-butyl)-3,4-dihydro-1,2,3-triazolo[4,5-b]pyridin-5-one Prepared as for Example 21, step b using cesium carbonate in place of potassium carbonate. Flash column chromatography on silica, eluting with 30% ethyl acetate-hexane, gave 3-(2,6-difluorophenyl)-6-(tert-butyl)-3,4-dihydro-1,2,3-triazolo[4,5-b]pyridin-5-one (0.086 g, 6%) as a white solid. $\delta_H$ (400 MHz; CDCl$_3$) 1.21 (9H, s), 7.20 (2H, t, J=9 and 9), 7.55–7.61 (1H, m), 8.03 (1H, s) and 12.70 (1H, s); m/z (ES+) 305 (M+H$^+$). Further elution with ethyl acetate gave 3-(2-fluoro-6-methoxyphenyl)-6-(tert-butyl)-3,4-dihydro-1,2,3-triazolo[4,5-b]pyridin-5-one (0.076 g, 5%) as a white solid. $\delta_H$ (400 MHz; CDCl$_3$) 1.23 (9H, s), 3.83 (3H, s), 6.91–6.97 (2H, m), 7.48–7.55 (1H, m), 7.99 (1H, s) and 12.00 (1H, s); m/z (ES+) 317 (M+H$^+$).

(c) 3-(2,6-Difluorophenyl)-6-(1,1-dimethylethyl)-5-(2-methyl-2H-1,2,4-triazol-3-ylmethoxy)-1,2,3-triazolo[4,5-b]pyridine Prepared as for Example 21, step c to give 3-(2,6-difluorophenyl)-6-(1,1-dimethylethyl)-5-(2-methyl-2H-1,2, 4-triazol-3-ylmethoxy)-1,2,3-triazolo[4,5-b]pyridine (0.024 g, 44%), m.p. 105–108° C. (EtOAc). $\delta_H$ (400 MHz; CDCl$_3$) 1.43 (9H, s), 3.81 (3H, s), 5.54 (2H, s), 7.21 (2H, dd, J=8 and 8), 7.50–7.60 (1H, m), 7.86 (1H, s) and 8.32 (1H, s); m/z (ES+) 400 (M+H$^+$).

EXAMPLE 32

6-(1,1-Dimethylethyl)-3-(2-fluoro-6-methoxyphenyl)-5-(2-methyl-2H-1,2,4-triazol-3-ylmethoxy)-1,2,3-triazolo[4,5-b]pyridine Prepared from 3-(2-fluoro-6-methoxyphenyl)-6-(tert-butyl)-3,4-dihydro-1,2,3-triazolo[4,5-b]pyridin-5-one (Example 31, step b) as for Example 21, step c to give 6-(1,1-dimethylethyl)-3-(2-fluoro-6-methoxyphenyl)-5-(2-methyl-2H-1,2,4-triazol-3-ylmethoxy)-1,2,3-triazolo[4,5-b]pyridine (0.033 g, 33%), m.p. 116–118° C. (Et$_2$O-hexane). Found: C, 57.95; H, 5.41; N, 23.56. $C_{20}H_{22}N_7O_2F.0.1(H_2O)$ requires C, 58.13; H, 5.41; N, 23.70. $\delta_H$ (400 MHz; CDCl$_3$) 1.44 (9H, s), 3.72 (3H, s), 3.78 (3H, s), 5.49 (2H, s), 6.93–6.98 (2H, m), 7.48–7.58 (1H, m), 7.83 (1H, s) and 8.29 (1H, s); m/z (ES+) 412 (M+H$^+$).

EXAMPLE 33

5-(2-Methyl-2H-1,2,4-triazol-3-ylmethoxy)-3-phenyl-1,2,3-triazolo[4,5-c]isoquinoline (a) 3-Phenyl-1,2,3-triazolo[4,5-c]isoquinolin-5-one n-Butyllithium (1.6 M, 7.5 ml, 12 mmol) was added dropwise at −78° C. over 5 min to a stirred solution of methyl 2-cyanomethylbenzoate (*Tetrahedron Lett.*, 1991, 32, 4133–4134) (2.10 g, 12 mmol) in dry THF (50 ml) under nitrogen. The deep red solution was stirred at −78° C. for 10 min, followed by the addition of a solution of phenyl azide (1.47 g, 12.3 mmol) in dry THF (10 ml). The green solution was stirred at −78° C. for 1.5 h then warmed to r.t. over 30 min, becoming bright blue. Saturated aqueous ammonium chloride (50 ml) was added and the mixture was acidified to pH 5 with 1M citric acid. The white precipitate was collected and washed with water and diethyl ether, then dried to give 3-phenyl-1,2,3-triazolo[4,5-c]isoquinolin-5-one (2.00 g, 64%). $\delta^H$ (360 MHz; DMSO) 7.58–7.68 (4H, m), 7.80–7.84 (2H, m), 7.93 (1H, ddd, J=8, 8 and 1), 8.30 (2H, d, J=8) and 12.80 (1H, s); m/z (ES+) 263 (M+H$^+$).

(b) 5-(2-Methyl-2H-1,2,4-triazol-3-ylmethoxy)-3-phenyl-1,2,3-triazolo [4,5-c]isoquinoline A mixture of 3-phenyl-1,2,3-triazolo[4,5-c]isoquinolin-5-one (0.10 g, 0.38 mmol), cesium carbonate (0.33 g, 1.0 mmol) and 2-methyl-3-chloromethyl-1,2,4-triazole hydrochloride (0.08 g, 0.48 mmol) in dry DMF (2 ml) was stirred at 60° C. for 5 h. The mixture was diluted with water (20 ml) and the white solid was collected, washing with water (10 ml) and diethyl ether (10 ml). The solid was dried to give 5-(2-methyl-2H-1,2,4-triazol-3-ylmethoxy)-3-phenyl-1,2,3-triazolo[4,5-c]isoquinoline (0.093 g, 68%), m.p. 188–190° C. Found: C, 63.48; H, 4.19; N, 27.14. $C_{19}H_{15}N_7O.0.1(H_2O)$ requires C, 63.54; H, 4.27; N, 27.30. $\delta_H$ (360 MHz; CDCl$_3$) 3.99 (3H, s), 5.83 (2H, s), 7.48–7.53 (1H, m), 7.61–7.70 (3H, m), 7.94–7.98 (2H, m), 8.20–8.22 (2H, m), 8.37 (1H, d, J=8) and 8.69 (1H, d, J=8); m/z (ES+) 358 (M+H$^+$).

EXAMPLE 34

5-(2-Ethyl-2H-1,2,4-triazol-3-ylmethoxy)-3-phenyl-1,2,3-triazolo[4,5-c]isoquinoline Prepared as for Example 33, step b using 2-ethyl-3-chloromethyl-1,2,4-triazole in place of 2-methyl-3-chloromethyl-1,2,4-triazole to give 5-(2-ethyl-2H-1,2,4-triazol-3-ylmethoxy)-3-phenyl-1,2,3-triazolo[4,5-c]isoquinoline as a white solid (0.095 g, 67%), m.p. 192–195° C. (Et$_2$O). Found: C, 64.45; H, 4.55; N, 26.20. $C_{20}H_{17}N_7O$ requires C, 64.68; H, 4.61; N, 26.40. $\delta_H$ (360 MHz; CDCl$_3$) 1.48 (3H, t, J=7), 4.31 (2H, q, J=7), 5.83 (2H, s), 7.48–7.52 (1H, m), 7.60–7.69 (3H, m), 7.93–7.98 (2H, m), 8.22–8.25 (2H, m), 8.45 (1H, d, J=8) and 8.68 (1H, d, J=8); m/z (ES+) 372 (M+H$^+$).

EXAMPLE 35

3-Phenyl-5-(2-propyl-2H-1,2,4-triazol-3-ylmethoxy)-1,2,3-triazolo[4,5-c]isoquinoline Prepared as for Example 33, step b using 2-propyl-3-chloromethyl-1,2,4-triazole in place of 2-methyl-3-chloromethyl-1,2,4-triazole to give 3-phenyl-5-(2-propyl-2H-1,2,4-triazol-3-ylmethoxy)-1,2,3-triazolo[4,5-c]isoquinoline as a white solid (0.088 g, 60%), m.p. 154–156° C. (Et$_2$O). Found: C, 53.02; H, 5.96; N, 20.50. $C_{21}H_{19}N_7O.5(H_2O)$ requires C, 53.05; H, 6.15; N, 20.62. $\delta_H$ (360 MHz; CDCl$_3$) 0.90 (3H, t, J=7), 1.92 (2H, qt, J=7 and 7), 4.21 (2H, t, J=7), 5.83 (2H, s), 7.48–7.52 (1H, m), 7.61–7.69 (3H, m), 7.93–7.98 (2H, m), 8.22–8.25 (2H, m), 8.34 (1H, d, J=8) and 8.69 (1H, d, J=8); m/z (ES+) 386 (M+H$^+$).

EXAMPLE 36

5-(1-Methyl-1H-1,2,4-triazol-3-ylmethoxy)-3-phenyl-1,2,3-triazolo[4,5-c]isoquinoline Prepared as for Example 33, step b using 1-methyl-3-chloromethyl-1,2,4-triazole in place of 2-methyl-3-chloromethyl-1,2,4-triazole to give 5-(1-methyl-1H-1,2,4-triazol-3-ylmethoxy)-3-phenyl-1,2,3-triazolo[4,5c]isoquinoline as a white solid (0.117 g, 86%), m.p. 189–190° C. (Et$_2$O). Found: C, 61.16; H, 4.44; N, 26.11. $C_{19}H_{15}N_7O.0.8(H_2O)$ requires C, 61.38; H, 4.50; N, 26.37. $\delta_H$ (360 MHz; CDCl$_3$) 3.96 (3H, s), 5.77 (2H, s), 7.42–7.48 (1H, m), 7.59–7.65 (3H, m), 7.91 (1H, dd, J=8 and 8), 8.08 (1H, s), 8.36–8.38 (2H, m), 8.45 (1H, d, J=8) and 8.65 (1H, d, J=8); m/z (ES+) 358 (M+H$^+$).

EXAMPLE 37

3-Phenyl-5-(pyridin-2-ylmethoxy)-1,2,3-triazolo[4,5-c]isoquinoline

Prepared as for Example 33, step b using 2-picolyl chloride hydrochloride in place of 2-methyl-3-chloromethyl-1,2,4-triazole hydrochloride to give 3-phenyl-5-(pyridin-2-ylmethoxy)-1,2,3-triazolo[4,5-c]isoquinoline as a white solid (0.080 g, 59%), m.p. 147–150° C. (Et$_2$O). Found: C, 70.58; H, 4.23; N, 19.34. $C_{21}H_{15}N_5O.0.25(H_2O)$ requires C, 70.48; H, 4.37; N, 19.57. $\delta_H$ (360 MHz; CDCl$_3$) 5.83 (2H, s), 7.25–7.30 (1H, m), 7.42–7.48 (1H, m), 7.56–7.62 (3H, m), 7.95 (1H, dd, J=8 and 8), 8.23 (2H, d, J=8), 8.52 (1H, d, J=8) and 8.68–8.70 (2H, m); m/z (ES+) 354 (M+H$^+$).

What is claimed is:

1. A compound of formula I, or a salt thereof:

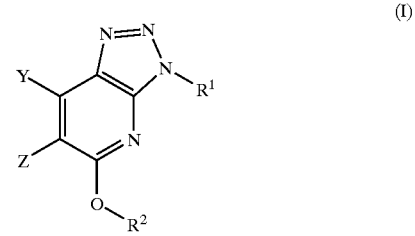

wherein

Y represents hydrogen or $C_{1-6}$ alkyl;

Z represents a group selected from furyl or thienyl, which group may be optionally substituted with 1–2 independent $C_{1-6}$ alkyl, aryl($C_{1-6}$)alkyl, halogen, halo($C_{1-6}$)

alkyl, cyano, cyano($C_{1-6}$)alkyl, hydroxy, hydroxymethyl, $C_{1-6}$ alkoxy, $C_{3-7}$ cycloalkyl($C_{1-6}$) alkoxy, $C_{3-7}$ cycloalkoxy, amino($C_{1-6}$)alkyl, di($C_{1-6}$) alkylamino($C_{1-6}$)alkyl, or di($C_{1-6}$)alkylaminocarbonyl ($C_{1-6}$)alkyl substituents;

$R^1$ represents $C_{3-7}$ cycloalkyl, or phenyl, any of which groups may be optionally substituted with 1–2 independent $C_{1-6}$ alkyl, aryl($C_{1-6}$)alkyl, halogen, halo($C_{1-6}$) alkyl, cyano, cyano($C_{1-6}$)alkyl, hydroxy, hydroxymethyl, $C_{1-6}$ alkoxy, $C_{3-7}$ cycloalkyl($C_{1-6}$) alkoxy, $C_{3-7}$ cycloalkoxy, amino($C_{1-6}$)alkyl, di($C_{1-6}$) alkylamino($C_{1-6}$)alkyl, or di($C_{1-6}$)alkylaminocarbonyl ($C_{1-6}$)alkyl substituents; and $R^2$ represents 1,2,4-triazolyl($C_{1-6}$)alkyl optionally substituted with 1–2 independent $C_{1-6}$ alkyl, aryl($C_{1-6}$)alkyl, halogen, halo($C_{1-6}$)alkyl, cyano, cyano($C_{1-6}$)alkyl, hydroxy, hydroxymethyl, $C_{1-6}$ alkoxy, $C_{3-7}$ cycloalkyl ($C_{1-6}$)alkoxy, $C_{3-7}$ cycloalkoxy, amino($C_{1-6}$)alkyl, di($C_{1-6}$)alkylamino($C_{1-6}$)alkyl, or di($C_{1-6}$) alkylaminocarbonyl($C_{1-6}$)alkyl substituents.

2. A compound as claimed in claim 1 represented by formula IIA, or a salt thereof:

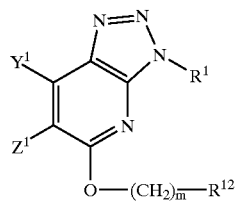

(IIA)

wherein $Y^1$ represents hydrogen or methyl;

$Z^1$ represents furyl, thienyl or chloro-thienyl;

$R^1$ is as defined in claim 1;

m is 1 or 2; and $R^{12}$ represents 1,2,4-triazolyl optionally substituted with $C_{1-6}$ alkyl, aryl($C_{1-6}$)alkyl, halogen, cyano, cyano($C_{1-6}$) alkyl, hydroxy, hydroxymethyl, $C_{1-6}$ alkoxy, $C_{3-7}$ cycloalkyl($C_{1-6}$)alkoxy, amino($C_{1-6}$)alkyl, di($C_{1-6}$) alkylamino($C_{1-6}$)alkyl, or di($C_{1-6}$)alkylaminocarbonyl ($C_{1-6}$)alkyl.

3. A compound as claimed in claim 2 represented by formula IIB, or a pharmaceutically acceptable salt thereof:

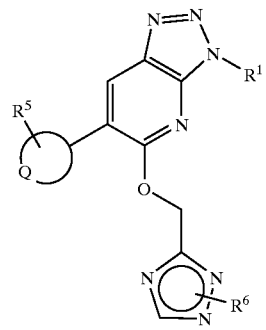

(IIB)

wherein

Q represents a furyl or thienyl ring;

$R^5$ represents hydrogen; and $R^6$ represents hydrogen, methyl, ethyl or n-propyl.

4. A compound selected from:

3-(2-fluorophenyl)-5-(2-methyl-2H-1,2,4-triazol-3-ylmethoxy)-6-(thien-3-yl)-1,2,3-triazolo[4,5-b]pyridine;
3-(2-fluorophenyl)-5-(2-methyl-2H-1,2,4-triazol-3-ylmethoxy)-6-(thien-2yl)-1,2,3-triazolo[4,5-b]pyridine;

or a salt thereof.

5. A compound selected from:

3-(2-fluorophenyl)-6-(2-furyl)-5-(2-methyl-2H-1,2,4-triazol-3-ylmethoxy)-1,2,3-triazolo[4,5-b]pyridine;
3-(2-fluorophenyl)-6-(3-furyl)-5-(2-methyl-2H-1,2,4-triazol-3-ylmethoxy)-1,2,3-triazolo[4,5-b]pyridine;
3-(2-fluorophenyl)-5-(1-methyl-1H-1,2,4-triazol-3-ylmethoxy)-6-(3-thienyl)-1,2,3-triazolo[4,5-b]pyridine;
3-(2-fluorophenyl)-5-(1-methyl-1H-1,2,4-triazol-3-ylmethoxy)-6-(2-thienyl)-1,2,3-triazolo[4,5-b]pyridine;
3-(2,6-difluorophenyl)-5-(2-methyl-2H-1,2,4-triazol-3-ylmethoxy)-6-(3-thienyl)-1,2,3-triazolo[4,5-b]pyridine;
3-(2,6difluorophenyl)-6-(3-furyl)-5-(2-methyl-2H-1,2,4-triazol-3-ylmethoxy)-1,2,3-triazolo[4,5-b]pyridine;

or a salt thereof.

6. A pharmaceutical composition comprising an effective amount of active compound of formula I as defined in claim 1 or a pharmaceutically acceptable salt thereof in association with a pharmaceutically acceptable carrier.

7. A method for the treatment of anxiety, which comprises administering to a patient in need of such treatment an effective amount of a compound of formula I as defined in claim 1 or a pharmaceutically acceptable salt thereof.

* * * * *